United States Patent
Gower et al.

(10) Patent No.: US 7,547,449 B2
(45) Date of Patent: Jun. 16, 2009

(54) METHOD FOR TREATING A BONE DEFECT WITH AN ORGANIC/INORGANIC COMPOSITE

(75) Inventors: Laurie B. Gower, Gainesville, FL (US); Matthew J. Olszta, Gainesville, FL (US); Elliot P. Douglas, Gainesville, FL (US); Sivakumar Munisamy, Fords, NJ (US); Donna L. Wheeler, Fort Collins, CO (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 354 days.

(21) Appl. No.: 11/433,725

(22) Filed: May 12, 2006

(65) Prior Publication Data
US 2006/0204581 A1  Sep. 14, 2006

Related U.S. Application Data

(60) Division of application No. 10/691,002, filed on Oct. 22, 2003, now Pat. No. 7,514,249, which is a continuation-in-part of application No. 10/418,843, filed on Apr. 18, 2003, now Pat. No. 7,514,248.

(60) Provisional application No. 60/373,801, filed on Apr. 18, 2002.

(51) Int. Cl.
*A61F 2/00* (2006.01)
*A61K 9/00* (2006.01)
*C12N 5/00* (2006.01)
*C12N 11/00* (2006.01)
*C12N 11/14* (2006.01)
*C12N 11/02* (2006.01)
*C12N 11/10* (2006.01)
*C12N 11/12* (2006.01)
*C12N 11/08* (2006.01)

(52) U.S. Cl. .................. 424/426; 424/400; 424/484; 424/93.7; 435/174; 435/176; 435/177; 435/178; 435/179; 435/180; 435/182

(58) Field of Classification Search .................. None
See application file for complete search history.

(56) References Cited

U.S. PATENT DOCUMENTS

| 4,774,227 | A | 9/1988 | Piez et al. |
|---|---|---|---|
| 4,795,467 | A | 1/1989 | Piez et al. |
| 4,865,602 | A | 9/1989 | Smestad et al. |
| 4,880,610 | A | 11/1989 | Constantz |
| 5,147,507 | A | 9/1992 | Gill |
| 5,178,845 | A | 1/1993 | Constantz et al. |
| 5,273,964 | A | 12/1993 | Lemons |
| 5,418,222 | A | 5/1995 | Song et al. |
| 5,455,231 | A | 10/1995 | Constantz et al. |
| 5,532,217 | A | 7/1996 | Silver et al. |
| 5,593,488 | A | 1/1997 | Wu |
| 5,800,541 | A | 9/1998 | Rhee et al. |
| 6,071,336 | A | 6/2000 | Fairchild et al. |
| 6,190,633 | B1 | 2/2001 | Takahashi et al. |
| 6,201,039 | B1 | 3/2001 | Brown et al. |
| 6,300,315 | B1 | 10/2001 | Liu |
| 6,592,712 | B2 | 7/2003 | Koukoulas et al. |
| 6,627,170 | B2 | 9/2003 | Takahashi et al. |
| 6,995,013 | B2 | 2/2006 | Connelly et al. |
| 2003/0059362 | A1 | 3/2003 | Takahashi et al. |
| 2003/0094252 | A1 | 5/2003 | Sundar et al. |
| 2004/0020410 | A1 | 2/2004 | Gane et al. |
| 2004/0052865 | A1 | 3/2004 | Gower et al. |
| 2005/0152990 | A1 | 7/2005 | Gower et al. |

FOREIGN PATENT DOCUMENTS

| EP | 0 143 363 B1 | 6/1985 |
|---|---|---|
| EP | 0 233 770 B1 | 5/1990 |
| EP | 0 197 693 B1 | 10/1991 |
| EP | 0 270 254 B1 | 3/1993 |
| EP | 03/035127 A1 | 5/2003 |

(Continued)

OTHER PUBLICATIONS

Addadi, L. and S. Weiner "Control and Design Principles in Biological Mineralization" *Angew. Chem. Int. Ed. Engl.* 1992, 31:153-169.

(Continued)

*Primary Examiner*—David M Naff
(74) *Attorney, Agent, or Firm*—Saliwanchik, Lloyd & Saliwanchik

(57) ABSTRACT

The subject invention concerns a composite comprising an organic fluid-swellable, fibrous matrix, such as collagen, and a mineral phase, such as calcium carbonate or phosphate mineral phase, for use as a biomimetic of bone. In another aspect, the subject invention concerns a process for making a composite involving the inclusion of acidic polymers to a supersaturated mineralizing solution, in order to induce an amorphous liquid-phase precursor to the inorganic mineral, which is then absorbed (pulled by capillary action) into the organic matrix. Advantageously, once solidified, a high mineral content can be achieved, with the inorganic mineral crystals embedded within the collagen fibers (intrafibrillarly) and oriented such that they are aligned along the long axes of the fibers of the organic matrix, thereby closely mimicking the natural structure of bone. The present invention further concerns a method of treating a patient suffering from a bone defect by applying a biomimetic composite to the bone defect site.

13 Claims, 12 Drawing Sheets

FOREIGN PATENT DOCUMENTS

WO     WO 03/089022 A1     10/2003

OTHER PUBLICATIONS

Addadi, L. et al. "A Chemical Model for the Cooperation of Sulfates and Carboxylates in Calcite Crystal Nucleation: Relevance to Biomineralization" *PNAS USA*, May 1, 1987, 84(9):2732-2736.

Addadi, L. et al. "Growth and Dissolution of Organic Crystals with 'Tailor-Made' Inhibitors—Implications in Stereochemistry and Materials Science" *Angew. Chem. Int. Ed. Engl.*, 1985, 24:466-485.

Addadi, S. and S. Weiner "Interactions between Acidic Proteins and Crystals: Stereochemical Requirements in Biomineralization" *PNAS USA*, Jun. 15, 1985, 82(12):4110-4114.

Aizenberg, J. "Patterned crystallization of calcite in vivo and in vitro" *J. Crystal Growth*, 2000, 211:143-148.

Bianco, P. "Structure and Mineralization of Bone" in Calcification in Biological Systems, Bonnuci, E., Ed., Chapter 11, pp. 243-268, 1992, CRC Press, Inc., Boca Raton, FL.

Bradt, J-H. et al. "Biomimetic Mineralization of Collagen by Combined Fibril Assembly and Calcium Phosphate Formation" *Chem. Mater.*, 1999, 11:2694-2701.

Carlson, S.J. "Vertebrate Dental Structures" in Skeletal Biomineralization: Patterns, Processes and Evolutionary Trends Carter, J.G., Ed., Chapter 21, pp. 531-556, 1990, Van Nostrand Reinhold, New York, NY.

Deng, Y. et al. "Study on the three-dimensional proliferation of rabbit articular cartilage-derived chondrocytes on polyhydroxyalkanoate scaffolds" *Biomaterials*, 2002, 23:4049-4056.

Dickinson, R.B. et al. "Biased Cell Migration of Fibroblasts Exhibiting Contact Guidance in Oriented Collagen Gels" *Annals. Biomed. Engin.*, 1994, 22:342-356.

Francillon-Vieillot, H. et al. "Microstructure and Mineralization of Vertebrate Skeletal Tissues" in Skeletal Biomineralization: Patterns, Processes and Evolutionary Trends Carter, J.G., Ed., Chapter 20, pp. 471-530, 1990, Van Nostrand Reinhold, New York, NY.

Gower, L. and D. Odom "Deposition of calcium carbonate films by a polymer-induced liquid-precursor (PILP) process" *J. Crystal Growth*, 2000, 210:719-734.

Gower, L. and D. Tirrell "Calcium carbonate films and helices grown in solutions of poly(aspartate)" *J. Crystal. Growth*, 1998, 191:153-160.

Gower, L. "The Influence of Polyaspartate Additive on the Growth and morphology of Calcium Carbonate Crystals" Doctoral Dissertation, 1997, University of Massachusetts at Amherst.

Greenfield, E.M. et al. "Ionotropic Nucleation of Calcium Carbonate by Molluscan Matrix" *Amer. Zool.*, 1984, 24:925-932.

Guido, S. and R. Tranquillo "A methodology for the systematic and quantitative study of cell contact guidance in oriented collagen gels" *J. Cell Sci.*, 1993, 105:317-331.

Jones, D. and U. Walter "The Silicate Garden Reaction in Microgravity: A Fluid Interfacial Instability" *J. Colloid and Interface Sci.*, 1998, 203:286-293.

Katz, E.P. et al. "The Structure of Mineralized Collagen Fibrils" *Connective Tissue Res.*, 1989, 21:149-158.

Landis, W.J. et al. "Mineral and Organic Matrix Interaction in Normally Calcifying Tendon Visualized in Three Dimensions by High-Voltage Electron Microscopic Tomography and Graphic Image Reconstruction" *J. Struct. Biol.*, 1993, 110:39-54.

Landis, W.J. et al. "Topographic Imaging of Mineral and Collagen in the Calcifying Turkey Tendon" *Connective Tissue Res.*, 1991, 25:181-196.

Mann, S. "Mineralization in Biological Systems" *Structure and Bonding*, 1983, 54:125-174.

Mann, S. "Crystallochemical Strategies in Biomineralization" in Biomineralization: Chemical and Biochemical Perspectives, Mann, S et al., Eds., Chapter 2, pp. 35-62, 1989, VCH Publishers, New York, N.Y.

Murthy, N.S. "Liquid Crystallinity in Collagen Solutions and Magnetic Orientation of Collagen Fibrils" *Biopolymers*, 1984, 23:1261-1267.

Nehrer, S. et al. "Chondrocyte-seeded collagen matrices implanted in a chondral defect in a canine model" *Biomaterials*, 1998, 19:2313-2328.

Oh, Y.R. and O.O. Park "Transient Flow Birefringence of Calf Skin Collagen Solutions" *J. Chem. Eng. Jpn.*, 1992, 25(3):243-250.

Olszta, M.J. et al. "A New Paradigm for Biomineral Formation: Mineralization via an Amorphous Liquid-Phase Precursor" *Connective Tissue Res.*, 2003, 44(Suppl. 1):326-334.

Olszta, M. "Biomimetic Mineralization of Collagen for Nanostructured Composites" poster materials, Jun. 2001, Department of Materials Science and Engineering, University of Florida, Gordon Research Conference.

Sciadini, M.F. et al. "Evaluation of Bovine-Derived Bone Protein with a Natural Coral Carrier as a Bone-Graft Substitute in a Canine Segmental Defect Model" *J. Orthopaedic Res.*, 1997, 15:844-857.

Sivakumar, M. and K Panduranga Rao "Preparation, characterization and in vitro release of gentamicin from coralline hydroxyapatite-gelatin composite microspheres" *Biomaterials*, 2002, 23:3175-3181.

Tranquillo, R.T. et al. "Magnetically oriented tissue-equivalent tubes: application to a circumferentially orientated media-equivalent" *Biomaterials*, 1996, 17:349-357.

Traub, W. et al. "Origin of Mineral Crystal Growth in Collagen Fibrils" *Matrix*, 1992, 12:251-255.

Traub, W. et al. "Three-Dimensional Ordered Distribution of Crystals in Turkey Tendon Collagen Fibers" *PNAS USA*, Dec. 15, 1989, 86(24):9822-9826.

Weiner, S. et al. "Lamellar Bone: Structure-Function Relations" *J. Struc. Biol.*, 1999, 126:241-255.

Weiner, S. and W. Traub "Bone structure: from ångstroms to microns" *FASEB J.*, 1992, 6:879-885.

Weiner, S. and W. Traub "Organization of Crystals in Bone" in Mechanisms and Phylogeny of Mineralization in Biological Systems, Suga, S. and Nakahara, H., Eds., Chapter 2.21, pp. 247-253, 1991.

Zhang, R. and P. Ma "Poly(a-hydroxyl acids)/hydroxyapatite porous composites for bone-tissue engineering. I. Preparation and morphology" *J. Biomed. Mater. Res.*, 1999, 44:446-455.

Zung, G. et al. "Tissue engineering in cardiovascular surgery: MTT, a rapid and reliable quantitative method to assess the optimal human cell seeding on polymeric meshes" *Euro. J. Cardio-thoracic Surg.*, 1999, 15:519-524.

Kikuchi, M. et al. "Preparation of hydroxyapatite/collagen composites using biomimetic process and their biocompatibility" *Mat. Res. Soc. Symp. Proc.*, 2000, 599:51-53.

Roveri, N. et al. "Biologically inspired growth of hydroxyapatite nanocrystals inside self-assembled collagen fibers" *Mat. Sci. Eng.*, 2003, 23(3):441-446 (abstract).

Gower, L. et al. "The influence of templates on mineralization via a precursor process" presented Aug. 12, 2002 at Gordon Research Conference (GRC), New London, New Hampshire.

Gower, L. et al. "Biomimetic bone" presented at ACERS 28th Int. Cocoa Beach Conference on Advanced Ceramics and Composites, Jan. 28, 2004, Cocoa Beach, FL.

Gower, L. "Biomimetic processing of ceramic composites" presented at CIMTEC-10th International Ceramics Congress and 3rd Forum on New Materials, Jul. 14-18, 2002, Florence, Italy.

Gower, L. "A new paradigm for biomineral formation" presented at 7th Int. Conf.—The Chemistry and Biology of Mineralized Tissues, Nov. 4-9, 2001, Sawgrass, FL.

Lee, I. et al. "Nanoparticle-directed crystallization of calcium carbonate" *Adv. Mater.*, 2001, 12(21):1617-1620.

Olszta, M.J. et al. "Synthesis of nano-fibrous $CaCO_3$ through a solution-precursor-solid (SPS) process" presented Apr. 7, 2003 at Materials Research Society (MRS) Spring Meeting, San Francisco, California.

Olszta, M.J. and L. Gower "Biomimetic composites using a polymer-induced liquid-precursor (PILP) process" presented Jun. 2002 at Annual Society for Experimental Mechanics (SEM) meeting, Milwaukee, Wisconsin.

Olszta, M.J. et al. "Scanning electron microscopic analysis of the mineralization of type I collagen via a polymer-induced liquid-precursor (PILP) process" *Calcif. Tissue Int.*, 2003, 72(5):583-591, Epub date Mar. 6, 2003.

Olszta, M.J. "Biomimetic mineralization of type-I collagen" presented at 7th Int. Conf.—The Chemistry and Biology of Mineralized Tissues, Nov. 4-9, 2001, Sawgrass, FL.

Olszta, M.J. et al. "Mimicking the nanostructured architecture of bone" presented at Fall Materials Research Society (MRS), Session L: Continuous Nanophase and Nanostructured Materials, Dec. 1-5, 2003, Boston, MA.

Olszta, M.J. "Biomimetic mineralization of type-I collagen" presented at UEF Biomimetic Engineering Conference, Mar. 3-7, 2002, Destin, FL.

Olszta, M.J. et al. "Biomimetic mineralization of type I collagenous matrices" presented at MRS Spring Meeting Proceedings, Symposium O-Materials Inspired by Biology, Apr. 21-25, 2003, San Francisco, CA.

Gower, L. "A model of biomineralization: Polymer-induced liquid-precursor (PILP) process" presented at Workshop on Investigation of Biomineralization Employing Model Systems, DFG Priority Programm 1117 Principles of Biomineralization, Braunschweig, Germany, Sep. 23-24, 2003.

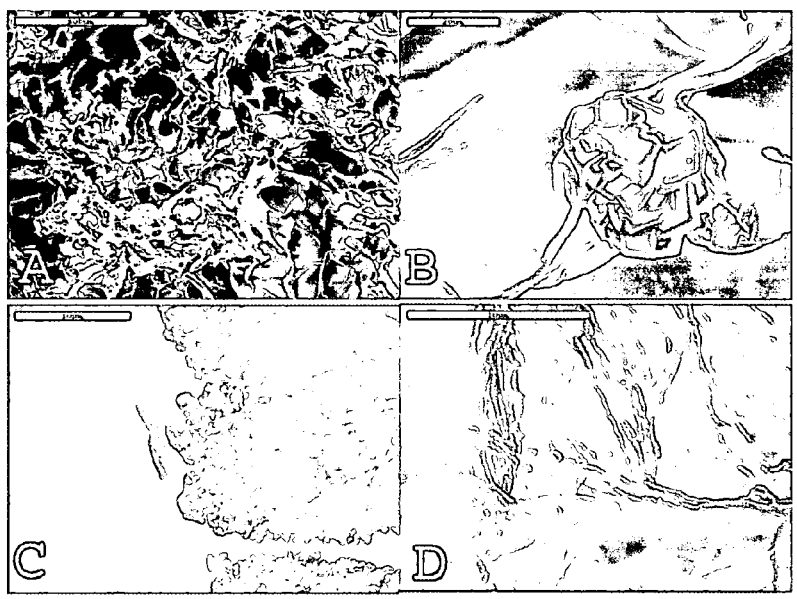
FIG. 6A  FIG. 6B
FIG. 6C  FIG. 6D
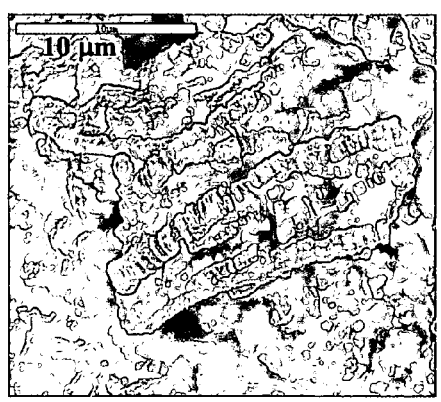
FIG. 8A  FIG. 8B
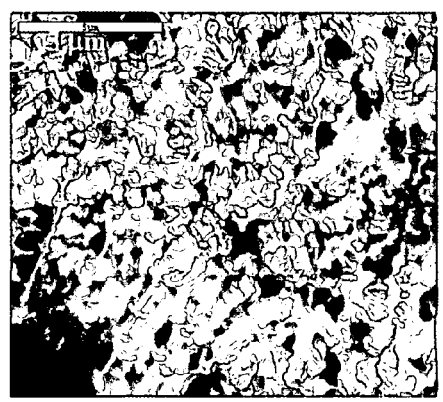
FIG. 8C

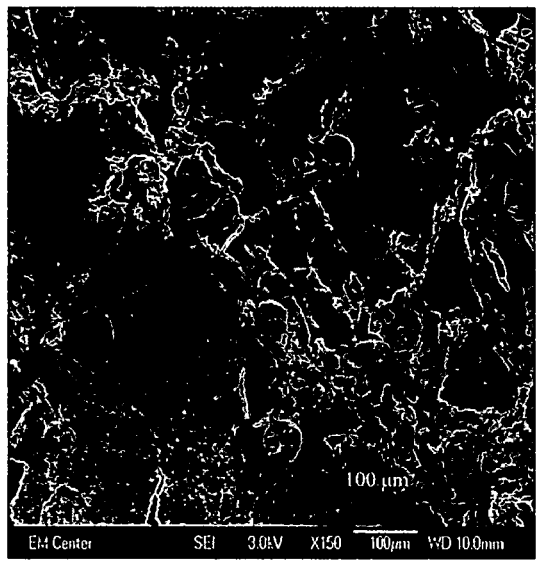 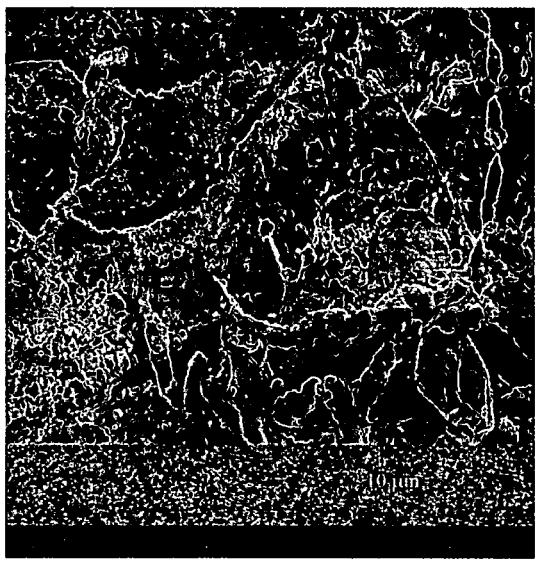
FIG. 20A    FIG. 20B
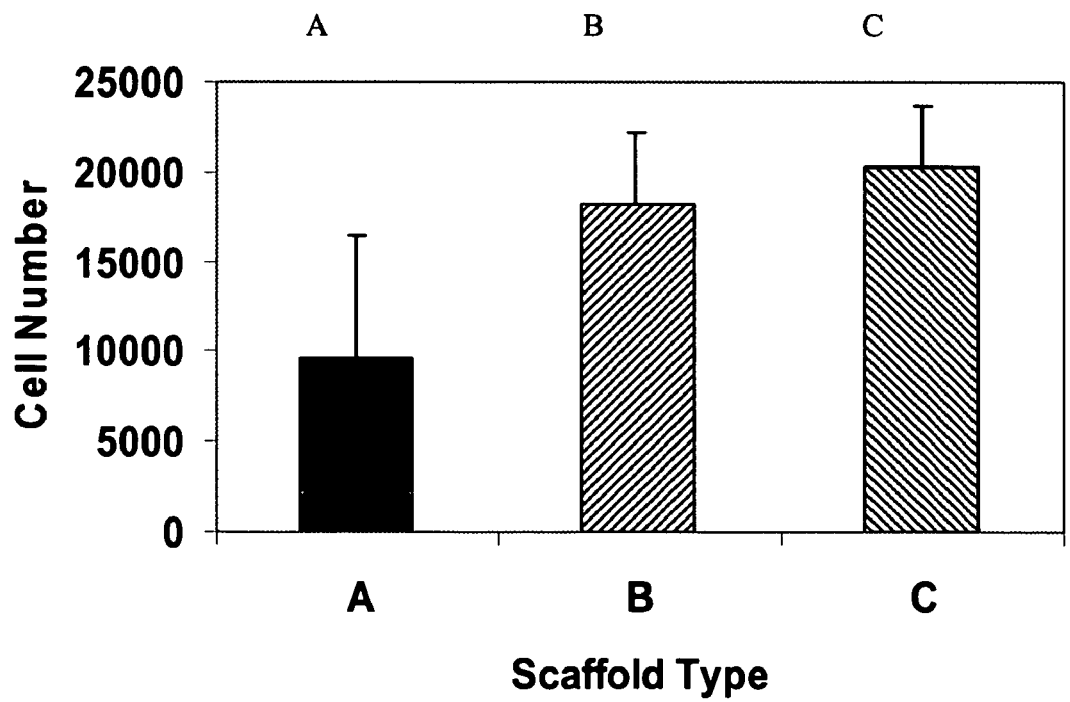
FIG. 21

METHOD FOR TREATING A BONE DEFECT WITH AN ORGANIC/INORGANIC COMPOSITE

CROSS-REFERENCE TO RELATED APPLICATIONS

The present application is a divisional of U.S. application Ser. No. 10/691,002, filed Oct. 22, 2003, now U.S. Pat. No. 7,514,249 which is a continuation-in-part of U.S. application Ser. No. 10/418,843, filed Apr. 18, 2003, now U.S. Pat. No. 7,514,248 which claims the benefit of U.S. Provisional Application No. 60/373,801, filed Apr. 18, 2002, which are hereby incorporated by reference in their entirety, including all figures, tables, and drawings.

GOVERNMENT SUPPORT

The subject invention was made with government support under a research project supported by National Science Foundation Grant No. ECS-9986333. The government has certain rights in this invention.

BACKGROUND OF THE INVENTION

Synthetic bone graft material made to closely resemble natural bone would be a useful replacement for natural bone. Acceptable synthetic bone can avoid the problem of availability and harvesting of autogenous bone and the risks and complications associated with allograft bone, such as risks of infection, disease, and viral transmission.

Natural bone is a composite material consisting of both water and organic and inorganic solid phases. Bone has a hard structure because its organic extracellular collagenous matrix is impregnated with inorganic crystals, principally hydroxyapatite ($Ca_{10}(PO_4)_6(OH)_2$). Calcium and phosphate account for roughly 65% to 70% of the bone's dry weight. Collagen fibers compose approximately 95% of the extracellular matrix and account for 25% to 30% of the dry weight of bone. The organic material gives bone its flexibility and resilience, while the inorganic material gives bone its strength and rigidity (modulus), and the organization of the two phases provides a high degree of toughness to the composite. A thorough review of bone structure from the angstrom level (mineral crystal) to the micron level (lamellae) has been presented (Weiner, S. et al. [1992] *FASEB*, 6:879-885).

Surrounding the mineralized collagen fibers is a ground substance consisting of protein-polysaccharides, or glycosaminoglycans, primarily in the form of proteoglycan macromolecules. The glycosaminoglycans serve to cement together the various layers of mineralized collagen fibers. The individual collagen molecules self-assemble to form triple helices, which assemble into collagen fibrils, which then assemble into microscopic fibers. Within the packing of the collagen fibrils/fibers are distinct gaps, sometimes called hole zones. These hole zones are created by the staggered arrangement of tropocollagen molecules (triple helical rods), which leads to periodicity of the hole and overlap zones. Various models have been proposed where these hole zones are completely isolated from each other, or are contiguous and together form a groove. Within these hole zones, mineral crystals form. The mineral crystals in final form nucleate and grow within the fibrils (intrafibrillar mineralization), as well as into the interstitial spaces (interfibrillar mineralization) (Landis, W. J. et al. [1993] *J. Struc. Biol.* 110:39-54). The mineral crystals in final form are a carbonated apatite mineral (dahllite), but initially may form as an amorphous calcium phosphate phase, which then transforms into the apatite (or possibly via an octacalcium phosphate precursor, which naturally forms plates). The apatite platelets of bone are of nanoscopic dimensions (only a few unit cells thick), and are densely packed into the type I collagen fibrils due to the intrafibrillar mineralization mechanism, and are well oriented with their c-axis (in the [001] direction) parallel to the long axis of the collagen fibrils. Because of the nature of the packing, the orientation of the collagen fibrils will determine the orientation of the mineral crystals (Martin, R. B. et al. [1998] "Skeletal Tissue Mechanics", Springer-Verlag Publishers, New York, N.Y.).

There are numerous biocompatible artificial bone substitutes currently on the market. Of these substitutes, none successfully mimics the composite or microstructure of bone. For example, man-made ceramic composites have some of the desired properties of natural bone (such as matching of modulus), but are notoriously brittle and prone to cracking. By contrast, biological ceramics like bone and teeth resist cracking, with a high toughness and stiffness. It is the nanostructured architecture that leads to mechanical properties that are unique to bone, which are not readily duplicated by polymers (which are not strong or stiff enough), or ceramics (which are brittle and lack toughness, and usually not bioresorbable). These mechanical properties are important because of the body's natural repair processes, in which bone is a living tissue and the cells respond according to the stresses they sense in their surrounding tissue (according to Wolf's Law). If an implant material has too high of a modulus (stiffness), the cells tend to resorb the surrounding bone due to the phenomenon of stress shielding (the stiffer material carries more of the load than the surrounding bone).

A logical choice of materials for a synthetic bone substitute would be a collagen-hydroxyapatite composite; indeed, many have attempted to mineralize collagen in vitro, but the preparation of such a composite has been limited by the ability to achieve the high mineral loading that is attained biologically by intrafibrillar mineralization. An associated periodic contrast pattern is commonly observed by transmission electron microscopy (TEM) of collagen fibers (Carter, J. G. [1990] Skeletal Biomineralization: Patterns, Processes and Evolutionary Trends, Volume 1, Van Nostrand Reinhold Publishers, New York, N.Y.; Hodge, A. J. et al. [1963] "Recent studies with the electron microscope on ordered aggregates of the tropocollagen molecule", in Aspects of Protein Structure, Ramanchandran, G. N. (ed.), pp. 289-300, Academic Press, London, England; Katz, E. P. et al. [1989] *Connect. Tissue Res.*, 21:49-159). From tomographic imaging of naturally mineralizing turkey tendon (which is considered a model of secondary bone formation), there is evidence that the hydroxyapatite crystals first appear within the hole zones of collagen, and then spread throughout the fibrils, leading to the array of iso-oriented nanocrystals of highly organized hydroxyapatite [HAP] embedded within the organic matrix (Landis, W. J. et al. [1993] *Structural Biology*, 110:39-54; Landis, W. J. et al. [1991] *Connect. Tissue Res.*, 25:181-196). Alternatively, there has been evidence that the collagen fibers contain an amorphous substance during the early stages of bone formation, referred to by Bonnuci as an "inorganic substance in bands" (ISBs), which then crystallizes into the more commonly observed platy crystals (Bonnuci, E. *Calcification in Biological Systems* [1992] CRC Press Boca Raton, Fla.).

From a materials engineering perspective, the nanostructure of bone is intriguing and can be difficult to define. For example, it is not clear whether bone is more accurately characterized as a polymer-fiber-reinforced ceramic-matrix composite or a ceramic-nanoparticle-reinforced polymer-matrix composite. The two phases are so intimately linked that the mechanical properties are distinctly different than ceramics or polymers, and therefore are difficult to reproduce. To date, scientists do not have a complete understanding of how bone is formed, even at this most basic level of structure. However, it is likely that the nanostructured architecture plays a role in the toughness of bone. Obviously, cellular control is important in biomineralization, and in the case of bone, helps to build its hierarchical structure (i.e., lamellae and osteons), but even the physicochemical mechanism for generating this nano-architecture has not been elucidated. Because intrafibrillar mineralization does not occur simply by attempting to crystallize collagen in vitro using supersaturated solutions of HAP (crystals only nucleate heterogeneously on the surface of the collagen fibers), it is generally assumed that nucleating proteins must be present within the gaps of the collagen fibrils.

It is understood within the biomineralization community that acidic proteins can act as inhibitors to crystal nucleation or growth (Addadi, L. et al. [1987] *Proc. Natl. Acad. Sci. USA*, 84:2732-2736; Addadi, L. et al. [1992] *Angew. Chem. Int. Ed. Engl.* 31:153-169; Mann, S. et al. [1983] *Structure and Bonding*, 54:125-174; Mann, S. et al. [1989] "Crystallochemical Strategies in Biomineralization" in Biomineralization-Chemical and Biochemical Perspectives. Mann, S., Webb, J., and Williams, R. J. P. (eds.), 33-62 (VCH Publishers, N.Y., N.Y.)). In the case of crystal growth, it has been shown that selective inhibition of growth along stereospecific crystallographic planes can lead to a change in crystal morphology (Addadi, L. et al. *Angew. Chem. Int. Ed. Engl.*, 24:466-485). In at least a few cases, acidic proteins have been shown to promote crystal nucleation (Addadi, L. et al. [1987] *Proc. Natl. Acad. Sci. USA*, 84:2732-2736; Greenfield, E. M. et al. [1984] *Amer. Zool.*, 24:925-932). It has also been shown that if the inhibitory action of a macromolecule is not complete, certain conditions lead to the induction (stabilization) of an amorphous liquid-phase precursor (Gower, L. B. et al. [2000] *J. Crystal Growth*, 210(4):719-734), which can have a profound consequence on crystal morphology since transformation of an amorphous precursor does not proceed via the same mechanism as traditional solution crystal growth (Mann, S. et al. [1989] "Crystallochemical Strategies in Biomineralization" in Biomineralization-Chemical and Biochemical Perspectives. Mann, S., Webb, J., and Williams, R. J. P. (eds.), 33-62 (VCH Publishers, N.Y., N.Y.)). Certain features of this polymer-induced liquid-precursor (PILP) process suggest that this mechanism may occur during morphogenesis of calcium carbonate biominerals in invertebrates (Gower, L. A. [1997] "The Influence of Polyaspartate Additive on the Growth and Morphology of Calcium Carbonate Crystals," Doctoral Thesis, Department of Polymer Science and Engineering, University of Massachusetts at Amherst, 1-119).

It would be desirable to have the capability to synthetically prepare a bone graft substitute that matches both the chemical and mechanical properties of bone. Such a material would be both load-bearing (with the appropriate modulus, strength, and toughness), yet bioresorbable to allow for the body's own tissue repair process to regenerate natural bone.

BRIEF SUMMARY OF THE INVENTION

The subject invention concerns an organic/inorganic composite comprising an inorganic mineral phase deposited onto and within an organic matrix, which is useful as a biomimetic substitute for bone and other tissues. The organic matrix is fluid-swellable, fibrous, and is penetrated by the inorganic mineral phase while the inorganic mineral phase is in the form of an amorphous polymer-induced liquid-precursor (PILP) phase. Optionally, while in the liquid-precursor phase, the inorganic mineral penetrates and saturates the matrix, which can cause the matrix to swell. The fluid-swellable matrix can also include interstitial spaces and pores within the matrix structure, having the inorganic mineral deposited therein.

Preferably, the fluid-swellable matrix of the composite is a longitudinally aligned fibrous material, with the inorganic mineral deposited intrafibrillarly within the matrix, with the mineral phase aligned along the long axes of the fibers of the fluid-swellable matrix. More preferably, the organic substrate is collagen and the inorganic mineral is calcium phosphate, calcium carbonate, or a mixture thereof, wherein the inorganic mineral is deposited intrafibrillarly within the collagen substrate. Examples of suitable calcium-containing inorganic minerals that can be used for the organic/inorganic composites of the invention include, but are not limited to, calcium phosphate, calcium carbonate, hydroxyapatite, strontium carbonate, calcium sulfate, calcium oxalate, calcium oxide, magnesium-bearing calcium carbonate or phosphate, calcium sulfate, calcium oxalate, and magnesium-bearing calcium carbonate or phosphate, or any polymorphs of these minerals.

In another aspect, the subject invention concerns a process for making the composite described herein involving the inclusion of short-chained acidic polymers to a supersaturated mineralizing solution, in order to induce an amorphous liquid-phase precursor to the mineral, which is then pulled by capillary action into interstices of the organic matrix (thus infiltrating the organic substrate), and subsequently mineralizes via solidification and crystallization of the precursor phase.

By using a PILP phase, the process of the present invention permits superior infiltration of an inorganic mineral phase (such as calcium phosphate or calcium carbonate) into an organic matrix (such as collagen), closely mimicking the structure of natural bone, which is a composite of collagen and calcium phosphate. In addition to having the capability to be highly mineralized (thermogravimetric analysis indicates that the composites can contain 60% by weight mineral), the organic/inorganic composite of the present invention is biocompatible, bioresorbable, and capable of load-bearing applications, such as use as a bone-graft substitute in critical-sized osseous defects, or joint replacement (such as artificial hip replacement).

The organic substrate that is mineralized according to the process of the subject invention preferably comprises collagen fibrils. However, other fluid-swellable, fibrous materials, having organic molecules that assemble into a secondary (e.g., supramolecular) fiber structure having a high aspect ratio (length-to-diameter) sufficient to support alignment of the mineral phase can be used.

The present invention further concerns a method of treating a patient having a bone defect by applying a composite described herein to the site of the bone defect.

BRIEF DESCRIPTION OF DRAWINGS

FIG. 1A shows that the rib region of a sea urchin tooth (*Arbacia tribuloides*) contains magnesium bearing calcium carbonate "rods", 5-7 μm in diameter, embedded in an amorphous $CaCO_3$ matrix. FIG. 1B shows that the ultrastructure of enamel from a rat incisor is more complex because it is "woven" into a cross-ply architecture by the ameloblast cells. Of relevance is the non-equilibrium morphology of the crystals, which in the vertebrates are polycrystalline bundles of HAP, rather than single-crystalline calcite rods, as in the urchin tooth. This further supports the assertion that the PILP process plays a fundamental role in the morphogenesis of biominerals, both in the vertebrates and invertebrates.

FIG. 2A shows a SEM micrograph of solidified precursor droplets. The droplets appear to have only partially coalesced and may not have been as fluidic as is typical of the $CaCO_3$ PILP phase. FIG. 2B shows a TEM micrograph of early stage solidified PILP droplets (average size≈200 nm). Light scattering studies have shown that the PILP droplets (for $CaCO_3$) start out approximately 100 nm in diameter and grow steadily until they reach a size of a couple of microns (when they become visible by optical microscopy). FIG. 2C shows an EDS of the sample shown in FIG. 2A confirming that the PILP phase is composed of calcium and phosphate. The small C and O peaks suggest that carbonate may also be present, which is difficult to eliminate due to $CO_2$ in the atmosphere.

FIG. 4A shows that the sponge, as received (not mineralized), consists of an isotropic mesh of type-I collagen fibers. FIG. 4B shows that the control reaction, in which collagen was mineralized with $CaCO_3$ without the addition of polymer, shows large rhombohedral crystals of calcite which nucleated heterogeneously on the collagen. FIG. 4C shows that when the sponge was mineralized using the PILP process, very different morphologies were formed, in which patchy, thick calcitic films were deposited. FIG. 4D shows that at higher magnification, it can be seen that the thick film is actually composed of collagen fibers encased in mineral. Because the encasing mineral is solid, it does not dehydrate to as large an extent as the surrounding matrix of pure collagen upon vacuum treatment for SEM analysis; therefore, the film-like composite is much thicker than the surrounding non-mineralized region, and appears as a step. It is also evident that the mineral provides some protection against beam damage, which was not the case for the un-mineralized region, in which a crack formed just below the mineralized patch. Note-the speckled appearance of the mineral is typical of PILP products, in which some precursor droplets do not fully coalesce to form smooth films (Gower, L. B. and D. J. Odom *J. Crystal Growth* 2000, 210(4):719-734; Gower, L. A. and D. A. Tirrell *J. Crystal Growth* 1998, 191(1-2):153-160).

FIG. 5A shows that this bovine collagen fiber was only partly mineralized, yet the fiber did not densify upon dehydration, suggesting that some of the mineral had penetrated into the fiber, which holds the remaining non-mineralized sub-fibers in place (arrow). In both the bovine collagen and CELLAGEN sponge, banding patterns became apparent after mineralization, which are not observed in the fibers as received (see FIG. 4A). In this case, however, the bands are not composed of tablets, but rather by a slight blebbing of the mineral coating (bottom right of fiber). The spacing of the bands is much smaller, at a sub-micron size scale (unlike the dimensions of the collagen crimp shown for the tablets in FIG. 3). FIG. 5B shows that blebbing of the small collagen sub-fibers in the CELLAGEN sponge is very pronounced in this particular region, to the point of having a disc-like appearance, in which the discs are oriented perpendicular to the long axis of the fibers. The banding pattern here is robust enough to measure; the bands occur at approximately every 380 nm, which is approximately six times the 64 nm spacing of type I collagen.

FIGS. 6A-6D show SEM micrographs of DAVOL Ultrafoam sponges under different mineralization conditions. FIG. 6A shows DAVOL Ultrafoam, no treatment, as received showing pore size on the order of 2-100 μm in diameter. FIG. 6B shows DAVOL Ultrafoam mineralized in the absence of polymeric additives, in which 20 μm diameter calcite rhombohedrals nucleated on the surface of the sponge. FIG. 6C shows a partially mineralized section of DAVOL Ultrafoam mineralized in the presence of PAA (5100 MW, ALDRICH). FIG. 6D shows a fully mineralized section of DAVOL Ultrafoam mineralized in the presence of PAA (5100 MW, ALDRICH).

FIGS. 8A-8C show calcium phosphate mineralized CELLAGEN sponge etched with 0.1 N HCl for 15 minutes to remove surface encapsulating mineral. Results are similar to CELLAGEN sponge mineralized with $CaCO_3$.

FIG. 9A shows a BF image of a CELLAGEN sponge stained with 1% phosphotungstic acid in 0.1M PBS. A 67-70 nm characteristic collagen banding pattern is observed. FIG. 9B shows a diffraction pattern of stained collagen. Observed pattern is similar to transmitted beam pattern, as there are no diffraction spots. FIG. 9C shows a BF image of CELLAGEN sample mineralized with CaP mineral through the PILP mechanism. Notice the 50-70 nm round particles around and in the collagen fibril (arrows), which are believed to be PILP droplets adsorbed to the collagen. Bar=100 nm. FIG. 9D shows a typical diffraction pattern of mineralized collagen fibril. Notice strong diffraction peaks in the direction of the c-axis of the collagen fibril.

In FIG. 10A, each individual collagen fibril is encased in mineral. Bar=10 μm. FIG. 10B shows high magnification of mineralized fibril bundles observed using FEG-SEM. The platy/needle-like crystals appear to be oriented along the long axis of the fibril bundle (arrow). Bar=100 nm.

FIG. 11A shows BF image of mineralized fiber. Bar=200 nm. FIG. 11B shows a selected area diffraction (SAD) pattern of the middle of the fiber in FIG. 11A, indicating that the mineral is hydroxyapatite. Note that arcs for the (002) and (004) planes are oriented perpendicular to the long axis of the collagen fibril (marked with long arrow), indicating that the HA crystals are aligned with their c-axes parallel to the fiber (in the [001] direction). FIG. 11C shows a Weak-Beam Dark-Field TEM micrograph of the fiber in A, illuminating the crystals that generated diffraction from the (002) plane. Note the illuminated crystals are long and needle-like (or thin plates edge on) and oriented along the long axis of the collagen fibril. Bar=200 nm.

FIG. 13A shows an SEM of the mineralized collagen fibril imaged in the left panel of FIG. 12. Note the non-descript surface features of the collagen fibril. There appear to be no platy crystals on the surface, suggesting that the crystals illuminated by the PMDF TEM image in FIG. 11C are within the fiber (i.e. the collagen fibril is intrafibrillarly mineralized). Bar=100 nm. FIG. 13B shows Energy Dispersive Spectroscopic analysis of a point in the middle of the fibril in A. Note that the spectrum has been increased to highlight the Ca, P and O peaks which were drowned out by the large peaks from the Al SEM stub and the Cu TEM grid. The large C peak is an artifact of the amorphous carbon coating process used to prevent charging in SEM. FIG. 13C shows a Bright Field TEM image of a mineralized collagen fibril. Platy crystals can be seen along the long axis of the collagen fibril. Note the 64 nm banding pattern of type-I collagen fibril that appears perpendicular to the long axis of the collagen fibril (highlighted by the arrow). Bar=100 nm.

FIGS. 20A and 20B shows SEM images of mineralized CELLAGEN scaffolds (with polymer) after exposure to mineralized solution. FIG. 20A shows osteoblasts adhered to mineralized scaffold at a magnification of 150×. FIG. 20B shows an adhered osteoblast producing mineralization nodules at a magnification of 1000×.

FIG. 21 shows the number of cells adhering to the three different scaffold types after a three and a half hour exposure. The three types of scaffolds include A) unmineralized with 9,658 cells; B) mineralized without polymer with 18,223 cells; and C) mineralized with polymer with 20,296 cells.

DETAILED DISCLOSURE OF THE INVENTION

Figure 1A:
FIGS. 1A-1B show scanning electron micrographs (SEMs) of "fibrous" biomineral morphologies that occur in the teeth of invertebrates and vertebrates.
Figure 1B:

The composite of the present invention comprises an organic substrate and an inorganic mineral phase, useful as a biomimetic material of bone or other hard tissue. Thus, the composite of the subject invention is an organic/inorganic composite that is highly mineralized, with its organic and inorganic components intimately associated in a manner mimicking the structure of natural bone. The organic substrate is composed of a fluid-swellable, fibrous matrix, which is penetrated by the inorganic mineral phase while the inorganic mineral is in the form of a transient polymer-induced liquid-precursor phase (PILP) that subsequently solidifies. Advantageously, once solidified, the inorganic mineral is oriented such that it is aligned along (e.g., running substantially parallel with) the long axes of the fibers of the organic fluid-swellable, fibrous matrix, thereby closely mimicking the structure of natural bone.

Optionally, while in the liquid precursor phase, the inorganic mineral penetrates and saturates the matrix, which can cause the matrix to swell. The fluid-swellable, fibrous matrix can also have interstitial spaces and pores, having the inorganic mineral deposited therein.

The organic substrate that is mineralized with an inorganic phase according to the process of the subject invention is fibrous. In one embodiment, the fibrous organic substrate comprises collagen fibrils as a substantially parallel-fibered matrix. In one embodiment, the fibrous organic substrate is collagen. However, other fluid-swellable, fibrous materials, having organic molecules that assemble into a secondary (e.g., supramolecular) structure having a high aspect ratio (i.e., a fiber) sufficient to support alignment of the mineral phase can be used. For example, elastin, cellulose, chitin, chitosan, and/or the peptide-amphiphile nanofibers described by Hartgerink et al. (Hartgerink, J. D. et al., Science, 2001, 294:1684-1688; Hartgerink, J. D. et al., PNAS, 2002, 99(8): 5133-5138) can be mineralized using the methods of the present invention. The inorganic phase is preferably calcium phosphate, calcium carbonate, or a mixture thereof. Examples of suitable calcium-containing inorganic minerals that can be used for the organic/inorganic composites of the invention include, but are not limited to, calcium phosphate, calcium carbonate, hydroxyapatite, strontium carbonate, and calcium sulfate, calcium oxalate, calcium oxide, magnesium-bearing calcium carbonate or phosphate, or any polymorphs of these minerals.

As used herein, the term "fibrous" is intended to refer to organic fluid-swellable matrices having at least some fiber (high aspect ratio) component. The fibers can be of various lengths, diameters, and orientations (e.g., parallel, mesh, random). The terms "fibers" and "fibrils" are used interchangeably herein to refer to filamentous or thread-like matter and any sub-fibers that contribute to a larger fiber. The fibers can be produced by self-assembly or directed assembly of molecules through synthesis procedures. Other fibrous matrices can be found, for example, in Vincent, J. (Structural Biomaterials, Princeton University Press, Princeton, N.J., 1990, Chapter 3, pp. 73-91).

The composite of the subject invention has similar mechanical, chemical, and biological properties to normal human bone tissue; thus, representing a biomimetic of bone (emulating the structure and mechanisms of the biological tissue), without the shortcomings of current artificial bone-replacement materials. For example, once solidified and crystallized, the inorganic mineral phase of the composite of the present invention lacks the facets typically present in other artificially mineralized collagen composites. Therefore, the composite of the present invention more closely resembles the patterns of mineral deposition found in nature, such as in human bone. In addition, the composite of the subject invention does not have the disadvantages associated with using donor tissue, such as disease transfer, rejection, unknown resorption rate, and scarcity.

In another aspect, the subject invention concerns a process for making the composite described herein involving the inclusion of one or more acidic polymers to a supersaturated mineralizing solution, in order to induce an amorphous liquid-phase precursor to the mineral, which is then absorbed by capillary action into the fluid-swellable, fibrous matrix of the organic substrate, and subsequently solidifies and crystallizes into the mineral phase. Preferably, the acidic polymer is a short-chained acidic polymer. The process of the subject invention, which uses a polymer-induced liquid precursor (PILP), permits superior infiltration of the mineral phase into the organic phase, such that the mineral phase is intimately associated with the organic matrix. In composites having an organic matrix comprising fibrils, the mineral phase can be associated with the organic matrix to the extent that nanocrystals are embedded within the interstices of the fibrils. Thus, as used herein, the term "liquid-precursor" or "liquid-phase mineral precursor" refers to an inorganic mineral phase that is sufficiently fluid to infiltrate, or be absorbed by, the fluid-swellable matrix.

The process of the subject invention comprises contacting an acidic polymer, such as poly-L-aspartic acid and/or polyacrylic acid, with a mineralizing solution of a calcium-containing mineral, thereby forming a liquid-phase mineral precursor; and contacting an organic substrate with the liquid-phase mineral precursor, wherein the organic substrate is collagen or another fluid-swellable, fibrous material (such as peptide-amphiphile nanofibers). The calcium-containing mineralizing solution can contain, for example, calcium salt, calcium chloride, and/or calcium phosphate, or other calcium-containing minerals. The liquid-phase mineral precursor is fluidic and amorphous such that droplets of the precursor are drawn into the organic substrate by capillary action. The droplets coalesce into a continuous coating and are preferentially absorbed into any interstices present within the organic substrate. Advantageously, where the organic substrate is collagen, the liquid-phase mineral precursor is drawn into the gaps and grooves of the collagen fibrils. As used herein, the term "gap" refers to the interstitial space between abutting ends of fibrils. Contiguous gaps among adjacent fibrils are referred to herein as "grooves".

The polymeric additive stabilizes the amorphous precursor to the mineral that is in the form of a liquid or liquid-like viscosity. Upon solidification of the precursor, non-equilibrium (non-faceted) crystal morphologies are generated that are distinct from the crystals produced by other solution crystallization processes carried out under similar conditions without the polymeric additive. In particular, because of the fluidic nature of the precursor, many of the highly unusual morphologies associated with biominerals (such as biominerals "molded" within vesicular compartments or "extruded" into fibers), can readily be accomplished using the process of the present invention.

After having coated and infiltrated the organic substrate, the amorphous mineral precursor solidifies and crystallizes, and the overall composite densifies. In the case of collagen, the present inventors have observed that disk-shaped crystals can be left periodically spaced within the fibers at approximately 380 nm intervals, which correlates to approximately six times the natural gap spacing of collagen. Presumably, the gaps have aligned across the fiber to form grooves capable of mineralizing, or the mineral diffuses throughout the interstitial space of the matrix, and is not restricted to just the hole zones. Interstitial space refers to the space between macromolecular chains, or in the case of collagen, the space between the staggered array of tropocollagen rods. Therefore, in the case where calcium carbonate is the inorganic mineral, the result is a nanostructured composite with calcitic nanocrystals embedded within the collagen fibrils, in a similar fashion to natural bone.

One or more steps of the process of the subject invention can be repeated. Hence, sequential loading of the organic substrate with the inorganic mineral can be carried out, resulting in various degrees of mineralization of the organic substrate. The extent of mineralization can be determined using methods of polymer matrix analysis known to those of ordinary skill in the art, such as thermogravimetric analysis (TGA) and ash fractionation of the inorganic and organic phases. Preferably, the composite of the subject invention comprises about 25% to about 40% organic matrix (such as collagen or other fluid-swellable, fibrous material) and about 35% to about 50% mineral phase (such as calcium phosphate, calcium carbonate, or a mixture thereof), by volume. The remaining component (about 10% to about 40%) can be water and non-collagenous (glyco)proteins, for example. More preferably, the composite of the subject invention comprises about 30% to about 34% organic substrate, and about 40% to about 45% mineral phase, by volume. Most preferably, the composite of the subject invention comprises about 32% organic substrate, about 43% mineral phase, and about 25% water, by volume, similar to the composite of natural bone.

Using a polymer-induced liquid phase precursor, the process and composites of the present invention are distinguishable from known methods for mineralization of reconstituted collagen that yield only equilibrium calcite rhombohedral crystals that nucleate heterogeneously and grow only on the exterior surface of the fibers. Mineralization using the process of the subject invention permits infiltration of the mineral into the matrix structure of the organic substrate, as evidenced by the banding of the collagen fibers, which consists of calcitic disks lying perpendicular to the long axis of the collagen fibers. This banding pattern is somewhat periodic and occurs with a spacing of approximately 250 nm to 300 nm, which roughly corresponds to six times the natural 64 nm spacing of hole zones within biogenic tropocollagen (the spacing is likely disturbed due to reconstitution of the commercial Type-1 collagen; alternatively, the spacing may arise from diffusion-limited exclusion of impurities (e.g., collagen and acidic polymer) during the crystallization process). Without being bound by theory, it is presumed that the PILP mineralization process results from the ion-binding affinities of the short-chained acid polymer in conjunction with water retention and nucleation inhibition, such that a metastable ionic liquid-phase precursor is generated.

The liquid-phase precursor of the inorganic mineral can be produced using a variety of methods. For example, synthesis of a liquid-phase precursor of calcium carbonate has been described previously (Gower, L. B. and D. J. Odom *J. Crystal Growth* 2000, 210(4):719-734; Gower, L. A. [1997] "The Influence of Polyaspartate Additive on the Growth and Morphology of Calcium Carbonate Crystals," Doctoral Thesis, Department of Polymer Science and Engineering, University of Massachusetts at Amherst, 1-119; Gower, L. A. and D. A. Tirrell *J. Crystal Growth* 1998, 191(1-2):153-160), where the vapor diffusion of the decomposition products of crushed ammonium carbonate $(NH_4)_2CO_3$ into a solution containing calcium chloride $(CaCl_2)$ and one or more short-chain acidic polymer additives. Alternative methods can be used to gradually raise the supersaturation of the crystallizing solution, including direct addition of a carbonate containing solution to the calcium containing solution; or the escape of carbon dioxide gas from a saturated calcium bicarbonate solution (which produced by bubbling carbon dioxide into an aqueous solution containing the calcium carbonate salt). Supersaturation can also be raised using temperature, pH, or removal of inhibitory species. Similar methods can be used for the calcium phosphate system, although higher temperature (37° C.) is more favorable for decomposition of ammonium phosphate (or any derivations of ammonium phosphate, such as ammonium phosphate dibasic). In addition, the phosphate counterion can be produced using enzymes that cleave phosphate-containing moieties. According to the mineralization process of the subject invention, the organic substrate can then be contacted with the liquid-phase precursor of the inorganic mineral, such as calcium phosphate, calcium carbonate, hydroxyapatite, strontium carbonate, calcium sulfate, calcium oxalate, calcium oxide, magnesium-bearing calcium carbonate or phosphate, or any polymorphs of these minerals.

The process of the subject invention can be carried out under a variety of conditions. For example, in the case of an aqueous system, the process can be carried out at a temperature of about 0° C. to about 100° C. Preferably, the process is carried out at about 37° C., to match physiological conditions. The process can be carried out at a pH in the range of about 5 to about 10. Preferably, the process is carried out at a pH of about 7.0 to about 7.8 and 1 atm. More preferably, the process is carried out at a pH of about 7.4.

The type of reaction vessel or vessels utilized for preparing the composite of the subject invention, or their sizes, are not critical. Any vessel or substrate capable of holding or supporting the organic and inorganic phases so as to allow the reaction to take place can be used. Preferably, the supersaturation is gradually increased, allowing time for the acidic polymer to induce and stabilize the liquid-phase mineral precursor. It should be understood that, unless expressly indicated to the contrary, the terms "adding", "contacting", "mixing", "reacting", and grammatical variations thereof, are used interchangeably to refer to the mixture of reactants of the process of the present invention (e.g., acidic polymer additives, calcium-containing solution, and so forth), and the reciprocal mixture of those reactants, one with the other (i.e., vice-versa).

Where collagen is used as the organic phase of the composite of the subject invention, the collagen can be obtained from mineralized or unmineralized sources. Preferably, the collagen is obtained from an unmineralized collagen source. Therefore, the collagen may come from biological sources such as bone, tendons, skin, or the like. Preferably, the collagen involves a combination of three strands of $\alpha 2$ collagen chains. The collagen can be obtained from a young, intermediate, or mature animal, such as mammals or avians. Examples of convenient animal sources of collagen include chicken, turkey, bovine, porcine, or equine sources. The collagen can also be recombinant collagen, or artificially synthesized. Collagen of various types can be used as any of collagen types I-XX, or combinations thereof.

Fluid-swellable (and particularly water-swellable), fibrous materials other than collagen can also be utilized as organic substrates within the composites of the subject invention. For example, fibrous polysaccharides (such as chitin and cellulose) can be used. Other examples of fluid-swellable materials appropriate as organic substrates include elastin, chitosan, and peptide nano-fibers. Any fluid-swellable, fibrous material can be utilized as the organic substrate, provided that the material can swell sufficiently to absorb the liquid-phase mineral precursor and support alignment of the mineral phase along the long axes of the fibers. Preferably, the fluid-swellable, fibrous material is bioresorbable and/or biocompatible so that cells can infiltrate and grow within the composite and eventually remodel it into natural bone tissue. However, bioresorbability may not be necessary if the composite material is biocompatible and has sufficient mechanical properties for long-term or permanent application.

The fluid-swellable, fibrous matrix can be surface modified before, during, or after mineralization using any of a variety of means known in the art, such as plasma treatment, etching, ion implantation, radiation, electron beam, chemical functionalization, grafting, photopolymerization, adsorption, or combinations thereof.

One or more of a variety of acidic polymers, such as acidic short-chained polymers, can be utilized to initiate the amorphous liquid-phase mineral precursor, including different polymers and biological materials. Polyacrylic acid (PAA), polymethacrylates (PMA), sulfonated polymers, phosphorylated proteins, peptides and polymers, sulfated glycoproteins, polyaspartic acid, polyglutamic acid, polyaspartate, polyvinyl phosphate, and blends or copolymers of these materials, individually and in mixtures, can be utilized to induce the liquid-phase separation, for example. A range of polymer molecular weights can be suitable if the other variables of the crystallizing conditions are appropriately modified to generate the PILP phase. Preferably, molecular weights in the range of 2,000 to 15,000 g/mol enhance the ability to induce formation of the precursor.

The desired hardness of the composite of the subject invention can be achieved by varying the weight ratio of the organic phase (such as collagen) and the inorganic phase (such as calcium phosphate and/or calcium carbonate), and the physical nature of the phases (such as degree of crystallinity, density, fibrillar structure of matrix, etc.).

The composite of the subject invention can be applied as a film or coating on a substrate. The substrate can be composed of any material, such as metal, polymer, and/or ceramic materials (such as hip joints, knee joints, dental implants, spinal fusion cages, and bone fillers). The composite can also be formed by sequential formation of layers, in which the orientation of the polymer in adjacent layers may or may not be controlled, similar to a laminated composite.

The present invention further concerns a method of treating a patient having a bone defect by applying a composite described herein to the site of the bone defect. As used herein, the term "patient" refers to any human or non-human animal suffering from a bone defect. According to the method of the subject invention, a therapeutically effective amount of the composite can be applied at the site of a bone defect to partially or fully restore structural integrity to the bone. Once applied, the composite of the subject invention can function as a filler (or partial filler) or plug, to mend the bone defect. The amount to be applied will depend upon the size and nature of the bone defect, and the clinical outcome that is sought. The composite can be applied in a malleable form, for example, as a paste or putty, such that the administered composite takes the shape of the bone defect. Alternatively, the composite can be molded pre-cast into a desired shape (such as the shape of the defect) using polymer composite molding methods known to those of ordinary skill in the art, and the molded composite can be administered as a solid or semi-solid article. Thus, the size, volume, thickness, and shape of the molded article can be controlled, as desired. The composite can be applied in particulate form. According to the method of the subject invention, the composite can be applied so that it directly contacts existing bone adjacent to, or defining, the bone defect site, or the composite can be contacting another implant, or both.

The composite of the subject invention can be applied to the bone defect site as a liquid. Once applied, with a syringe for example, the liquid composite can coagulate or cure ("set") shortly after application to form a solid.

The composite of the subject invention can be used as a vehicle for the in situ delivery of biologically active agents. The biologically active agents incorporated into, or included as an additive within, the composite of the subject invention can include, without limitation, medicaments, growth factors, vitamins, mineral supplements, substances used for the treatment, prevention, diagnosis, cure or mitigation of disease or illness, substances which affect the structure or function of the body, or drugs. The biologically active agents can be used, for example, to facilitate implantation of the composite into a patient and to promote subsequent integration and healing processes. The active agents include, but are not limited to, antifungal agents, antibacterial agents, anti-viral agents, antiparasitic agents, growth factors, angiogenic factors, anaesthetics, mucopolysaccharides, metals, cells, and other wound healing agents. Because the processing conditions can be relatively benign (physiological temperature and pH), live cells can be incorporated into the composite during its formation, or subsequently allowed to infiltrate the composite through tissue engineering techniques.

As indicated above, cells can be seeded onto and/or within the organic/inorganic composites of the present invention. Likewise, tissues such as cartilage can be associated with the composites prior to implantation within a patient. Examples of such cells include, but are not limited to, bone cells (such as osteoclasts, osteoblasts, and osteocytes), blood cells, epithelial cells, neural cells (e.g., neurons, astrocytes, and oligodendrocytes), and dental cells (odontoblasts and ameloblasts). Seeded cells can be autogenic, allogenic, or xenogenic. Seeded cells can be encapsulated or non-encapsulated.

Examples of antimicrobial agents that can be used in the present invention include, but are not limited to, isoniazid, ethambutol, pyrazinamide, streptomycin, clofazimine, rifabutin, fluoroquinolones, ofloxacin, sparfloxacin, rifampin, azithromycin, clarithromycin, dapsone, tetracycline, erythromycin, cikprofloxacin, doxycycline, ampicillin, amphotericine B, ketoconazole, fluconazole, pyrimethamine, sulfadiazine, clindamycin, lincomycin, pentamidine, atovaquone, paromomycin, diclarazaril, acyclovir, trifluorouridine, foscarnet, penicillin, gentamicin, ganciclovir, iatroconazole, miconazole, Zn-pyrithione, and silver salts, such as chloride, bromide, iodide, and periodate.

Growth factors that can be incorporated into the composite of the present invention include, but are not limited to, bone growth factors (e.g., BMP, OP-1) basic fibroblast growth factor (bFGF), acidic fibroblast growth factor (aFGF), nerve growth factor (NGF), epidermal growth factor (EGF), insulin-like growth factors 1 and 2 (IGF-1 and IGF-2), platelet-derived growth factor (PDGF), tumor angiogenesis factor (TAF), vascular endothelial growth factor (VEGF), corticotropin releasing factor (CRF), transforming growth factors alpha and beta (TGF-$\alpha$ and TGF-$\beta$), interleukin-8 (IL-8), granulocyte-macrophage colony stimulating factor (GM-CSF), the interleukins, and the interferons.

Other agents that can be incorporated into the composite of the subject invention include acid mucopolysaccharides including, but not limited to, heparin, heparin sulfate, heparinoids, dermatan sulfate, pentosan polysulfate, chondroitin sulfate, hyaluronic acid, cellulose, agarose, chitin, dextran, carrageenin, linoleic acid, and allantoin.

Proteins that can be incorporated into, or included as an additive within, the composite of the subject invention include, but are not limited to, collagen (including cross-linked collagen), fibronectin, laminin, elastin (including cross-linked elastin), osteopontin, osteonectin, bone sialoproteins (Bsp), alpha-2HS-glycoproteins, bone Gla-protein (Bgp), matrix Gla-protein, bone phosphoglycoprotein, bone phosphoprotein, bone proteoglycan, protolipids, bone morphogenetic protein, cartilage induction factor, platelet derived growth factor and skeletal growth factor, enzymes, or combinations and biologically active fragments thereof. Other proteins associated with other parts of human or other mammalian anatomy can be incorporated or included as an additive, include proteins associated with cartilage, such as chondrocalcining protein, proteins associated with dentin, such as phosphoryin, glycoproteins and other Gla proteins, or proteins associated with enamel, such as amelogenin and enamelin. Agents incorporated into the composite of the subject invention may or may not facilitate or enhance osteoinduction. Adjuvants that diminish an immune response can also be used in conjunction with the composite of the subject invention.

The biologically active agents can first be encapsulated into microcapsules, microspheres, microparticles, microfibers, reinforcing fibers and the like to facilitate mixing and achieving controlled, extended, delayed and/or sustained release. Encapsulating the biologically active agent can also protect the agent against degradation during formation of the composite of the invention.

Additionally, the biologically active agents can be pendantly attached to the organic or inorganic phase. The attachment can be facilitated through covalently linking the agent to the organic or inorganic phase, or through the use of hydrogen bonding.

In a preferred embodiment of the invention, the biologically active agent is controllably released into a mammal when the composite of the invention is implanted into a mammal, due to bioresorption relying on the time scale resulting from cellular remodeling. Preferably, the composite of the subject invention is used to replace an area of discontinuity in the bone tissue in the mammalian body. The area of discontinuity in the bone can be as a result of trauma, disease, genetic defect, tumor, or surgery, for example.

The composite of the subject invention can be formulated into a variety of shapes suitable for its function as a bone graft substitute, such as a plate, pin, rod, screw, anchor, tack, arrow, staple, button, or other regular or irregular shape. The composite of the present invention can be formulated as a three-dimensional scaffold and, optionally, seeded with one or more cell types for implantation within a patient. For example, a highly mineralized, collagen/hydroxyapatite composite with a nanostructured architecture similar to parallel-fibered compact bone can be fabricated using the PILP process of the present invention. Using the method of the present invention, mineralized scaffolds with the composition and mechanical properties of bone can be produced. These scaffolds can exhibit osteoconductive properties that promote rapid infiltration of cells into the implant material for neovascularization and osseous ingrowth. Hence, the organic/inorganic composites produced by the methods of the present invention can be sufficiently osteoconductive, load-bearing, and bioresorbable so as to replace the current "gold standard", which requires harvesting of autogenous bone tissue.

The term "intrafibrillar", as used herein, is used to specify the location of the crystallites, which has been described as a "deck-of-cards" arrangement of iso-oriented nanocrystals that are embedded within any interstitial spaces within the organic matrix. For example, in the case of HA, the platy/needle-like crystals are oriented with the [001] direction of the crystal aligned parallel to the long axis of the collagen fibril. In the case of collagen, these interstitial spaces include the gaps and grooves of the assembled collagen fibrils (Traub, W. et al. [1992] *Matrix,* 12:251-255; Weiner, S. et al. [1991] "Organization of Crystals in Bone", in Mechanisms and Phylogeny of Mineralization in Biological Systems, Suga, S. and Nakahara, H. (eds.), pp. 247-253; Traub, W. et al., [1989] *Proc. Natl. Acad. Sci.,* 86:9822-9826, Springer-Verlag Publishers, New York, N.Y.). Thus, as used herein, intrafibrillar means that the amorphous precursor penetrates the fluid-swellable, fibrous matrix of the organic substrate, and mineral crystals grow on and within the matrix structure, and on and within any underlying substructure, such as fibers. The amorphous mineral phase penetrates the fibers (and fibrils, if present) of the fibrous substrate, and mineral crystals grow on and within the fibers (and fibrils, if present) of the organic substrate. As used herein, the term "interfibrillar" means that the mineral crystals grow within the fluid-swellable matrix, but do not necessarily penetrate the interior of the fibrillar substructure generated from the self-assembly of the organic molecules (e.g., tropocollagen molecules).

The term "bone defect", as used herein refers to any bone deficient region, such as a void, gap, recess, or other discontinuity in the bone. The bone defect can be artificially or naturally established, and can occur due to disease or trauma, for example. Thus, the bone defect can occur as a consequence of pathologic, inflammatory, or tumor diseases, surgical interventions, congenital defects, or bone fractures, and the like. For example, in the case of certain diseases, such as bone tumors, the bone defect is artificially established by removing the tumor tissue. Thus, according to the method of the subject invention, the composite can be applied, for example, to repair periodontal defects, for craniofacial reconstruction, joint reconstruction, fracture repair, to conduct orthopedic surgical procedures, and spinal fusion, for example. The term "bony defect" is also intended to include anatomical sites where augmentation to a bony feature is desired by the patient in the absence of disease or trauma, such as in elective cosmetic surgery. Thus, the "defect" can be one that is subjectively perceived by the patient, and where augmentation of the bone deficient region is desired.

The term "biocompatible", as used herein, means that the material does not elicit a substantial detrimental response in the host. It should be appreciated that when a foreign object is introduced into a living body, that the object may induce an immune reaction, such as an inflammatory response that will have negative effects on the host. As used herein, the term "biocompatible" is intended to include those materials that cause some inflammation and/or tissue necrosis, provided that these effects do not rise to the level of pathogenesis. Various assays known in the art can be utilized to assess biocompatibility. For example, the following assays can be conducted to determine biocompatibility of cells to the composites: alkaline phosphatase activity (e.g., using Diagnostic kit 245, SIGMA) for a particular cell phenotype (e.g., osteoblast), methylthiazol tetrazolium (MTT) proliferation assay (Zund G. et al. [1999] *European Journal Cardiothoracic Surgery* 15:519-524; Deng Y. et al. [2002] *Biomaterials* 23:4049-4056), histology/histomorphometry, and SEM analysis. Response variables for subsequent statistical analysis would include, for example, cell count, alkaline phosphatase expression, cell distribution, and cell/tissue penetration.

The term "biodegradable", as used herein, means capable of being biologically decomposed. A biodegradable material differs from a non-biodegradable material in that a biodegradable material can be biologically decomposed into units which may be either removed from the biological system and/or chemically incorporated into the biological system.

The term "bioresorbable", as used herein, refers to the ability of a material to be resorbed in vivo. "Full" resorption means that no significant extracellular fragments remain. The resorption process involves elimination of the original implant materials through the action of body fluids, enzymes, or cells. Resorbed calcium carbonate may, for example, be redeposited as bone mineral, or by being otherwise re-utilized within the body, or excreted. "Strongly bioresorbable", as the term is used herein, means that at least 80% of the total mass of material implanted is resorbed within one year.

The term "polymorph", as used herein, refers to inorganic minerals that are identical chemical compositions but different crystal structures.

The terms "comprising", "consisting of", and "consisting essentially of" are defined according to their standard meaning and may be substituted for one another throughout the instant application in order to attach the specific meaning associated with each term.

Materials and Methods

Polymer-Induced Liquid-Precursor (PILP) Process. The preparation of a PILP phase has been described previously (Gower, L. B. and D. J. Odom *J. Crystal Growth* 2000, 210 (4):719-734; Gower, L. A. [1997] "The Influence of Polyaspartate Additive on the Growth and Morphology of Calcium Carbonate Crystals," Doctoral Thesis, Department of Polymer Science and Engineering, University of Massachusetts at Amherst, 1-119; Gower, L. A. and D. A. Tirrell *J. Crystal Growth* 1998, 191(1-2):153-160). The general process introduces the acidic polymer into an aqueous salt solution which is slowly raised in supersaturation. One common method for raising supersaturation is to slowly introduce one of the ionic species, for example using a modified vapor diffusion technique developed by Addadi et al. (Addadi, L. et al. [1985] *Proc. Natl. Acad. Sci. USA*, 82:4110-4114), in which ammonium carbonate $(NH_4)_2CO_3$ vapor, produced by decomposition of its powder, diffuses into a solution containing calcium chloride $CaCl_2$ and the acidic polymeric additive. This multistage process is illustrated by the formula:

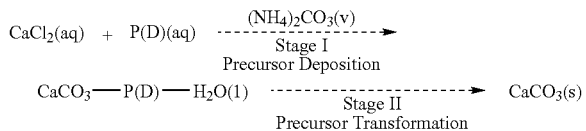

Figure 2A:
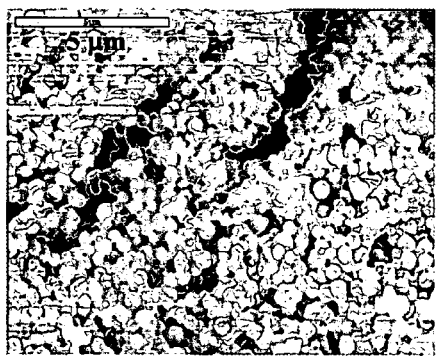
FIGS. 2A-2C show SEM, transmission electron microscopy (TEM) and energy dispersive spectroscopy (EDS) analyses of calcium phosphate PILP phase prepared with $CaCl_2$, poly(vinyl phosphonic acid) (PVPA) and polymer-assisted solution-phase (such as polyaspartic acid: PASP) additives.
Figure 2B:
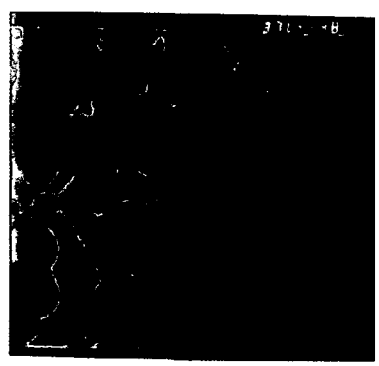

Alternatively, calcium phosphate (CaP) readily forms an amorphous gel prior to crystallization, which is unlike the PILP phase (a truly liquid-like material and has a distinct phase boundary that can be acted upon by capillary forces). In the case of bone formation, neither an amorphous solid or gel would be sufficiently fluidic to be drawn into the nanoscopic spaces of collagen, which is presumed necessary for leaving the matrix embedded with mineral precursor and ultimately nanocrystallites. However, as seen in the SEM and TEM images in FIGS. 2A and 2B, CaP "droplets" were generated using a combination of polyanionic additives (polyaspartate and polyvinyl phosphonate) as shown in the equation below.

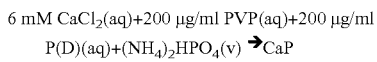

Figure 2C:
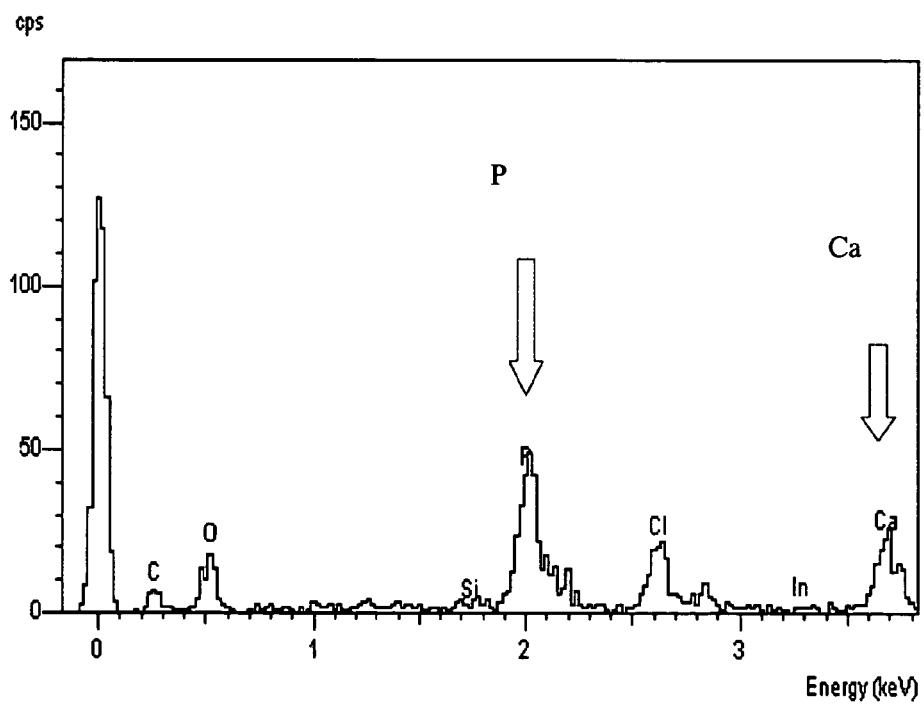

Energy dispersive spectroscopy (EDS) (FIG. 2C) and x-ray diffraction (XRD) were used to confirm composition and phase of the mineral, which was hydroxyapatite.

Typically, the crystal products are deposited onto a thin glass coverslip (22 mm D.) that is placed in the crystallizing solution, which can then be examined by polarized light microscopy (including in situ examination with ultra-long-working-distance objectives), or gold coated for scanning electron microscopy (SEM). The exact concentration of the reactants depends on the experiment, and is provided below.

Formation of Fibrous Crystals. The formation of fibrous calcium carbonate was accomplished by using the PILP process to deposit $CaCO_3$ on glass cover slips. The cover slips were cleaned by soaking overnight in a bath of 12N $H_2SO_4$/Nochromix solution, followed by a distilled water rinse, and a final rinse with ethanol. Each of the cover slips was placed in a Falcon polystyrene petri dish (3.5 cm D.), to which was added 2.7 mL of a filtered 9 mM $CaCl_2$ solution ($CaCl_2.2H_2O$, 98+% pure, SIGMA). Poly(aspartic acid) was added to a final concentration of 28 µg/ml (poly-L-aspartic acid-sodium salt, $M_w$ (vis)=35600, SIGMA), and distilled water was added to the petri dishes using a micropipette to bring the final volume to 3 mL. A control dish, containing no polymeric additives, was run in parallel with each of the experiments. All solutions were prepared with doubly distilled water and filtered using 0.2 µm GELMAN ACRODISC syringe filters. The dishes were covered with stretched parafilm, into which three holes were punched, and placed in a 10 dessicator. Vapor diffusion of ammonium carbonate was accomplished by adding three small vials (5 mL) of crushed ammonium carbonate (that had been covered with stretched parafilm and punched with one hole) in the dessicator with the calcium/polymer solutions. The dessicators were then held at room temperature (25° C.) for one week, at which time the glass slides were removed from the solution, rinsed in a small beaker of water and then ethanol. The glass slides were then examined using an Olympus BX-60 optical microscope in transmission mode, using crossed polars and an optional first-order-red wave plate.

Mineralization of Collagen with Calcium Carbonate. Three different collagen substrates were mineralized with $CaCO_3$: bovine collagen (type-I, insoluble from bovine Achilles tendon (ALDRICH), CELLAGEN sponge (ICN), which is also type-I collagen that is fabricated into 1 mm thick porous sponges, and AVITENE Ultrafoam hemostatic sponge, which is a type-I collagen sponge with 2-100 µm pores. Either 2-3 strands of fibrous bovine collagen, or ⅛"×¹⁄₁₆" strips of CELLAGEN sponge, were placed in the crystallizing dishes and the crystallization process was performed as described above. The bovine collagen was mineralized using a solution of 12 mM $CaCl_2$ and 200 µg/ml polyaspartic acid (poly-L-aspartic acid-sodium salt, $M_w$ (vis)=8600; SIGMA), followed by vapor diffusion of the carbonate. The CELLAGEN sponge was mineralized using 12 mM $CaCl_2$ and 200 µg/ml polyacrylic acid (polyacrylic acid-sodium salt, $M_w$ (vis)=5100; SIGMA). The mineralized collagen was removed from the solution, rinsed in a small beaker of water and then ethanol. The collagen samples were then examined using an OLYMPUS BX-60 optical microscope (in transmission mode, using crossed polars and an optional first-order-red wave plate) and subsequently Au/Pd coated and examined with a JEOL 6400 SEM instrument. The AVITENE Ultrafoam collagen was mineralized using the same procedure for mineralizing the CELLAGEN sponges by adding micromolar amounts ranging from 10-200 µm of polyaspartic acid (PAA, MW 5100, ALDRICH) and a calcium chloride solution. The mineralized AVITENE Ultrafoam collagen was crushed using a liquid $N_2$ mortar and pestal and put into solution. The solution was sampled and specimens placed on a copper TEM grid.

Mineralization of Collagen with Calcium Phosphate. CELLAGEN sponge (ICN), which is also a reconstituted type-I bovine collagen that is fabricated into a 1 mm thick porous sponge, was taken in strips of ⅛"×¹⁄₁₆" and placed in the crystallizing dishes and the crystallization process was performed as described above. The bovine collagen was mineralized using a solution of 6 mM $CaCl_2$ and 200 µg/mL of both polyaspartic acid (poly-L-aspartic acid-sodium salt, $M_w$ (vis) =8600 g/mol; SIGMA) and polyvinyl phosphonic acid (polyvinyl phosphonic acid, $M_w$ (vis)=20000; POLYSCIENCES), followed by vapor diffusion of ammonium phosphate dibasic (SIGMA). The mineralized collagen was removed from solution, rinsed in a small beaker of water and then ethanol. The collagen samples were then examined using an OLYMPUS BX-60 optical microscope (in transmission mode, using crossed polars and an optional first-order-red wave plate) and subsequently Au/Pd coated and examined with a JEOL 6400 SEM or JEOL 6330 FEGSEM instrument. The mineralized CELLAGEN collagen was crushed using liquid $N_2$ mortar and pestle and put into solution. The solution was samples and specimens placed on a copper TEM grid.

Acid Etch and Bleach Treatment. In order to determine the structure of the calcium carbonate deposited on the collagen fibers, and the extent of the mineral penetration (acid and bleach respectively), the mineralized composites were exposed to either a 0.1 N HCl solution (to etch mineral) or a 10% bleach solution (to degrade collagen) for 15 minutes at 23° C. After treatment, the samples were thoroughly rinsed in de-ionized water in order to avoid any contamination by the remaining acid or bleach.

Scanning Electron Micrograph (SEM) Analysis. The samples (untreated, acid etched and bleached) were dried under vacuum at 30-40° C. overnight and subsequently Au/Pd coated and examined with a JEOL 6400 SEM instrument. In addition to the mineralized samples, a control sample of as received CELLAGEN sponge was also coated and examined.

XRD Analysis. Three different samples, approximately 1×1 $cm^2$ were prepared for x-ray analysis. The first sample was as received, non-mineralized CELLAGEN, the second sample was mineralized without the presence of polymeric additive, and the third sample was mineralized for 7 days at 4° C. in the presence of µM quantities of PAA. The samples were run on a PHILIPS XRD 2500 at 40 KV and 20 mA. Since the crystal composite was not expected to vary between the 5 different samples mineralized in the presence of polymeric additive, the sample mineralized for 1 cycle was chosen for XRD analysis.

TEM Analysis. The AVITENE Ultrafoam hemostatic collagen samples were examined using a transmission electron microscope (TEM) in Brightfield (BF) and diffraction modes. TEM analysis. Both CELLAGEN and AVITENE Ultrafoam hemostatic sponge samples were examined using a transmission electron microscope (TEM) in Brightfield (BF), Poor Man's dark field (PMDF), and Selected Area Diffraction (SAD) modes.

EXAMPLE 1

Mineralization of Collagen with Calcium Carbonate

Figure 3A:
FIGS. 3A and 3B show SEMs of PILP-mineralized bovine collagen. The mineral precipitated predominantly as a coating on the fibers, but in some regions, as illustrated in FIGS. 3A and 3B, isolated platy tablets deposited along the fiber in a banded pattern. These bands of $CaCO_3$ tablets (composition verified by EDS) are perpendicular to the long axis of the collagen fiber (indicated with an arrow), and appear to be associated with the topography of the fiber (perhaps nucleated on the crimps).
Figure 3B:

The PILP mineralization of bovine Achilles tendon type-I collagen showed interesting results. The individual fibers of the bovine collagen became coated or encrusted by a film of $CaCO_3$. In some regions on the collagen fibers, the mineral film was patchy and in the form of isolated tablets (FIGS. 3A and 3B). Because there is a lack of facets in PILP formed crystals, energy dispersive spectroscopy was used to verify that these films and tablets are composed of $CaCO_3$. Interestingly, the $CaCO_3$ "tablets" appear to have preferentially deposited along the fibers in a banded pattern (FIGS. 3A & 3B). It is not clear if the PILP phase was deposited in those locations due to topography (such as defects or kinks along the crimped collagen backbone), or if some more specific templating interaction is occurring between the PILP phase and organic matrix.

Figure 4A:
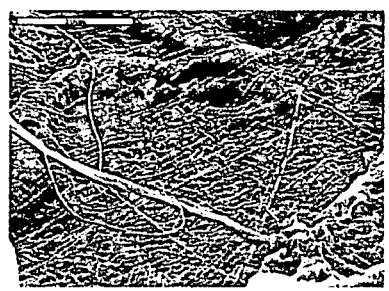
FIGS. 4A-4D show SEMs of mineralized CELLAGEN sponge.
Figure 4B:
Figure 4C:
Figure 4D:
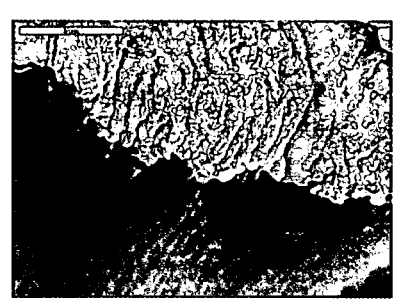

The CELLAGEN sponge (which is reconstituted bovine collagen) provides a better substrate onto which to deposit PILP phase because it has a flat and compact surface, as seen in the SEM photomicrograph of untreated CELLAGEN in FIG. 4A. Upon mineralization of the sponge without polymeric addition (FIG. 4B), large calcite crystals (~20-40 µm) grew on the surface of the sponge. Evidently collagen is a reasonably good substrate for heterogeneous nucleation of calcite. When the sponge was mineralized using the PILP process, by adding polymeric additive (polyacrylic acid in this case), the mineral phase deposited as a thick patchy film on the surface of the sponge (FIG. 4C). A higher magnification view of one of these patches shows that the individual collagen sub-fibers are coated or encased by the mineral (FIG. 4D), which is why the mineral coating appears to be so thick since it is actually a composite structure. It was noted that this mineral coating serves as a protective layer against beam damage during SEM observation. For example, FIG. 5D shows a crack that formed during SEM analysis on the non-mineralized region of the sponge (bottom half of the figure), which was halted by the mineralized portion (upper half of the figure). In addition, the mineral encased fibers exhibit charging without degradation, unlike the unprotected fibers.

Figure 5A:
FIGS. 5A and 5B show SEMs with banding patterns on mineralized collagens.
Figure 5B:
Figure 7:
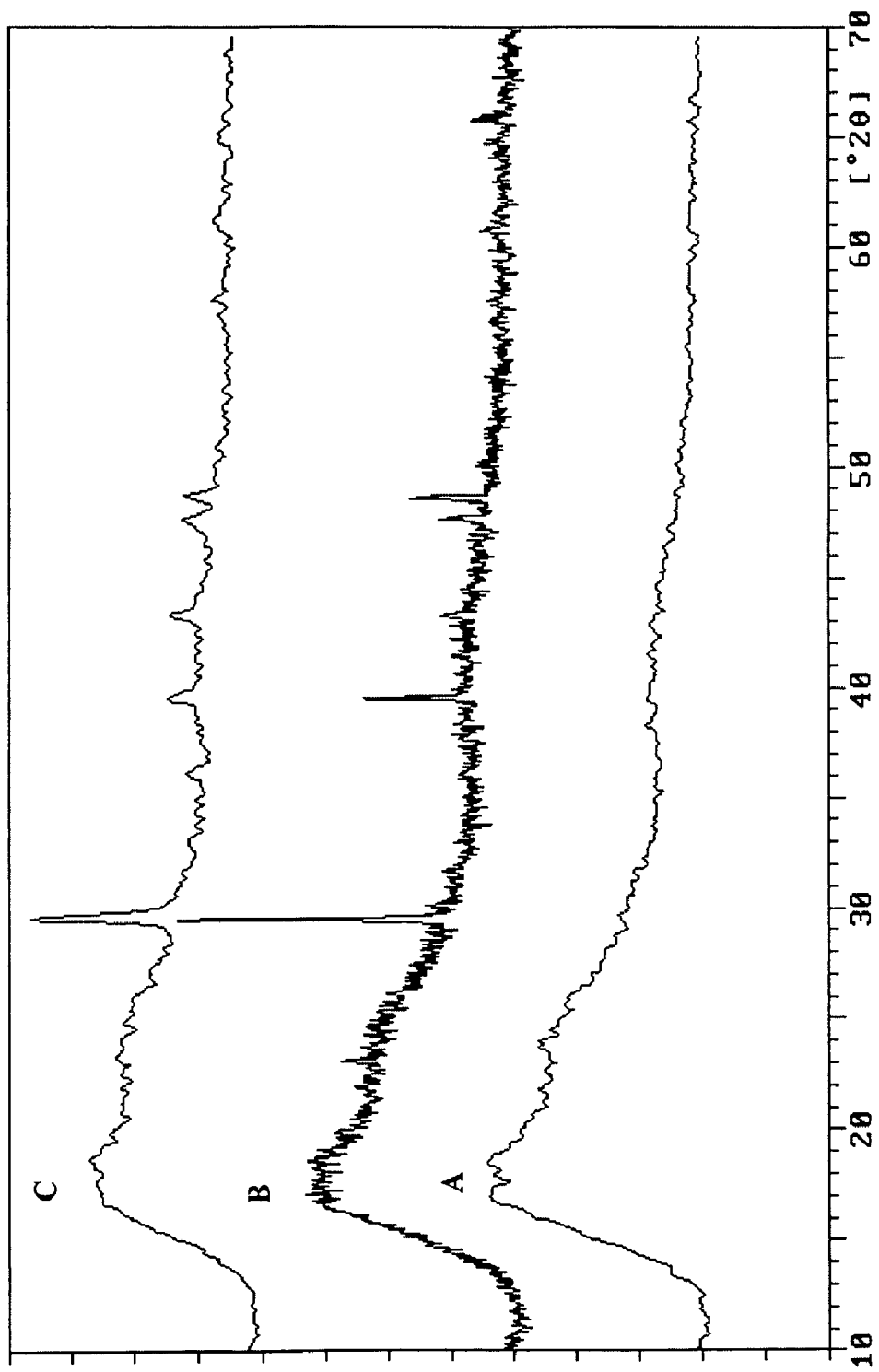
FIG. 7 shows X-ray diffraction (XRD) analysis, with Line A showing the diffraction pattern of dehydrated collagen sponge held in distilled water for three days, Line B showing the diffraction pattern of collagen sponge mineralized without polymer for three days in a supersaturated $CaCO_3$ solution, and Line C showing the diffraction pattern of collagen sponge mineralized for three days in a supersaturated solution of $CaCO_3$ containing acidic polymers. The characteristic calcitic peaks on Line B and Line C are in the same position. The peaks in Line C are much broader than those in Line B, suggesting that either there is strain in the crystals, or the crystals are of much smaller size as compared to those in Line B (Cullity, B. D., *"Elements of X-ray Diffraction"* [2001] Addison-Wesly Longman, N.Y.)

In FIGS. 5A and 5B, a periodic banding pattern can be seen on the mineral coatings of these fibers. In the mineralized bovine collagen shown in FIG. 5A, blebbing is apparent along the length of encapsulating mineral towards the end of the fiber. Unlike the banding pattern in FIGS. 3A and 3B, the spacing of the banding pattern here is submicron. At the top region of the photo, it can be seen that this fiber did not fully mineralize. The individual sub-fibers of the collagen became separated as they densified during sample dehydration (in preparation for SEM analysis) because the ends were restrained by the surrounding mineralized tissue. This would suggest that some amount of mineral is intercalating into the large fiber bundles and coating the individual sub-fibers.

In FIG. 5B, which is mineralized CELLAGEN sponge, the blebbing is so pronounced that disc-shaped entities appear along the whole length of the fibers. The relative periodicity of the blebbing (~380 µm) seems to suggest that it is somehow related to the periodicity of the swollen collagen fibers, yet the spacing between the bands is ~6 times the collagen hole-overlap periodicity (64 nm), but an order of magnitude less than the distance between the natural crimp in collagen (~1 µm-10 µm). The periodicity is not a precise match with native collagen; however, it is likely that the reconstituted collagen does not assemble into as precise a periodic structure as natural collagen. It is interesting that the encasement with mineral seems to capture this periodic structure, suggesting that perhaps the mineral is preferentially located in the gap zones of the collagen, which upon dehydration of the sample for SEM analysis, leaves those regions thicker than the surrounding regions containing less mineral and more organic matrix (which dehydrate and densify to a larger extent). Notably, Bradt et al. (Bradt, J. H. et al. [1999] *Chem. Mater.* 11:2694-2701) have deposited HAP on collagen in the presence of poly(aspartic acid) and found TEM evidence that some plate-like crystals of HAP were associated with the gaps in the collagen fibrils. Their results are interesting but it is likely that a more potent acidic protein will be required to fully generate a liquid-phase precursor for the calcium phosphate system.

PILP mineralization of the AVITENE ultrafoam hemostatic sponge yielded similar results to CELLEGEN sponge mineralization. Samples that were mineralized in the absence of polymeric additives showed simple calcite nucleation on the surface of the collagen (FIG. 6B). Upon addition of micromolar amounts of (10-200 µm) polyaspartic acid (PAA; MW 5100, ALDRICH), each individual collagen fiber appeared to be mineralized (FIGS. 6C and 6D). As with the CELLAGEN, there were sections that were partially mineralized (FIG. 6C) and those that were fully mineralized (FIG. 6D).

EXAMPLE 2

Mineralization of Collagen with Calcium Phosphate

The results for the CaP system were very similar to the $CaCO_3$ system, but with some differences in the mineral texture. The XRD spectrum of the mineralized collagen (not shown) shows peaks consistent with HA, although some peak shifts and differences in peak intensities are noted, which seem to suggest polymer-mineral interactions are prevalent (Sivakumar, M. et al. [2002] *Biomaterials*, 23(15):3175-3181). The mineralized CELLAGEN was also subjected to an acid etch treatment to remove excess mineral, and showed very similar results to the $CaCO_3$ composites. A periodic banding pattern is seen for the more protected mineral (FIGS. 8A and 8B), and crystals have a similar disk-like morphology. At this point, it is not clear if these are single crystals, or just thick clumps of remnant mineral phase. In some regions of the sample, the mineral remnants were less organized and the morphology was different, exhibiting a more platy shape (FIG. 8C). Without being bound by theory, it is presumed that these banding patterns are due to exclusion of impurities and shrinkage of the precursor phase during dehydration/solidification/crystallization, because similar incremental growth bands in non-templated mineral depositions have been observed.

Figure 9A:
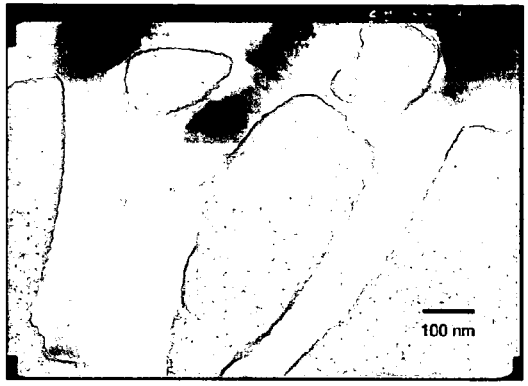
FIGS. 9A-9D show TEM, Bright Field (BF) and electron diffraction analyses of mineralized CELLAGEN experiments.
Figure 9B:
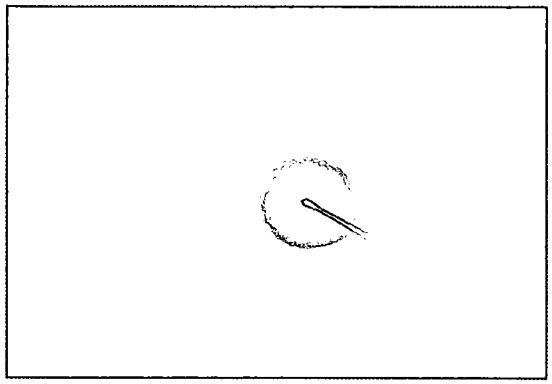
Figure 9C:
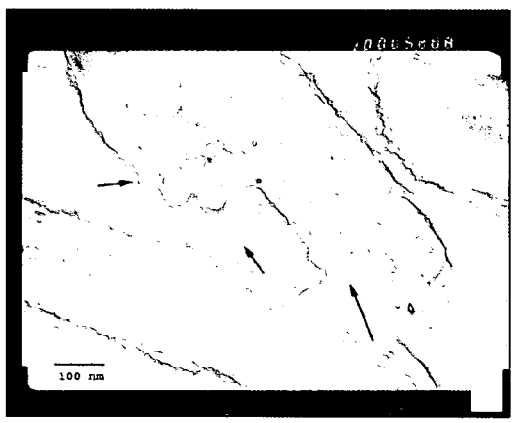
Figure 9D:
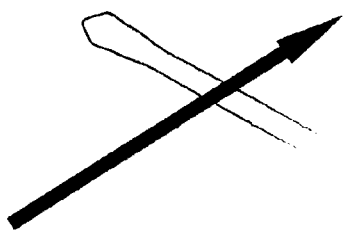

Using a cryogenic mortar and pestal, CELLAGEN sponges mineralized with CaP PILP phase were crushed into a fine powder using liquid nitrogen. The powder was then dispersed in ethanol and sonicated for 5 minutes. A small drop of the solution was then pipetted onto a copper TEM grid and stained using a 1% phosphotungstic acid in 0.1M PBS (ph 7.4). The grids were then examined using a transmission electron microscope (TEM). As observed in FIG. 9A, the unmineralized CELLAGEN sample (which was also prepared in the same manner as noted above), characteristic 67-70 nm quarter-staggered banding patterns appear in the bright field image. Since collagen is a pseudo-liquid crystalline polymer, there have been reports in the literature in which collagen has displayed a distinct diffraction pattern. Yet, in close agreement with the XRD diffraction patterns of CELLAGEN, the diffraction pattern of CELLAGEN in FIG. 9B shows a similar pattern to that of the transmitted beam. Unlike FIG. 9A, where there are only banding patterns present, in the bright field image of mineralized CELLAGEN, FIG. 9C, there are numerous black spots within the collagen. These black spots (1-5 nm) infer a higher electron adsorption, most often caused by crystalline materials. While there is a possibility of these spots being a deposition of phosphotunstic acid crystals, the larger (50-70 nm) round particles highlighted by arrows correlate well with SEM images of the CaP PILP phase (FIG. 2B), and thus are not believed to be a resultant of the stain. More interesting, however, are the diffraction patterns of the mineralized CELLAGEN sponge (FIG. 2D). Unlike the diffraction pattern of pure collagen (FIG. 9B), the selected area diffraction (SAD) of the mineralized fiber (FIG. 9C) shows distinct diffraction along the long axis of the fiber (indicated by arrow).

Based on these results, it has been observed that a combination of polymers with phosphate and carboxylate functionality elicits the PILP process in CaP. With the phosphate containing polymer alone, there is some evidence of PILP phase, but it appears to be less fluidic than when a combination of the two polymers is used. Therefore, polypeptides comprising controlled amounts of aspartic acid and serine residues (for subsequent phosporylation) using a solid-phase peptide synthesizer (ABI-433A) can be utilized. Fortunately, relatively low molecular weight (M.W.) polymers seem to be the most effective at inducing the PILP process (e.g., within the range of about 50 to about 75 residues), which makes this synthetic route amenable for preparing small amounts of the "mimetic proteins" of interest. The following series of polypeptides can be used for further studies, and based on the results of these studies, tailor-made polymers can be designed for further optimization: (i) homopolymer of polyserine, phosphorylated to different degrees (M.W.=5000 Da); (ii) alternating copolymer of Asp and Ser residues (with varying degrees of phosphorylation) (M.W.=5000 Da); (iii) alternating copolymer of Asp, Ala, PSer, for reduced polarity (M.W.=5000 Da); and block copolymer of Asp and Ser residues (with varying degrees of phosphorylation) (M.W.=5000 Da), block size of about 10 residues.

The polymers can then be examined under similar conditions that were used for the previous studies, with variable concentrations of the polymeric additive. Based on the findings of these studies, further optimization and trends can be determined using statistically designed experiments (with other factors to consider, such as: Ca concentration, rate of phosphate additions, polymer concentration and M.W., Mg-ion additive, carbonate additive, and temperature).

EXAMPLE 3

Crystallographic Orientation of Calcium Phosphate on Collagen Fibrils

A reconstituted collagen sponge (Cellagen., ICN Biomedicals Inc.), which is comprised of pure type-I bovine collagen, was mineralized with HA mineral using the PILP process. The process involved using a 1 mM $CaCl_2.2H_2O$ solution in combination with 200 μg/mL Poly(αβ-DL-Aspartic acid) (Polyasp) and 200 μg/mL Poly(vinyl phosphonic acid) (PVPA). The collagen sponge was cut into a 3×3 $cm^2$ sample and placed in the mineralizing solution. This solution was then placed, uncovered, in a desiccator with three equal sized petri dishes, uncovered, and filled with crushed diammonium hydrogen phosphate. Uncovered is stressed in this explanation because, in the $CaCO_3$ PILP process, all of the dishes are covered with parafilm into which three holes are punched to reduce the diffusion rate of the reactants. The ammonium carbonate decomposes much more rapidly than the ammonium phosphate; therefore, the reaction kinetics are decreased. The entire desiccator was then placed in an incubator set at 37° C. The ammonium phosphate slowly decomposed into the vapor phase and fed the phosphate counterion into the mineralizing solution. The samples were left to mineralize between 1-4 weeks, at which time they were removed from solution and rinsed in both water and ethanol to remove any soluble salts.

Samples were prepared for transmission electron microscopy (TEM) following the protocols performed on bone and naturally mineralized tendon by Weiner and Traub (Weiner, S. et al., *Journal of Structural Biology*, 1999, 126(3):241-255). This included crushing the samples into a nanometer powder in a liquid nitrogen mortar and pestle. A few small drops of ethanol were then placed on the powder, followed by drawing the slurry into a micropipette. The slurry was transferred to a 3 mm diameter carbon/Formvar coated copper TEM grid, followed by staining with 1% phosphotungstic acid (PTA) in a PBS buffer. The samples were then analyzed using a 200cx JEOL TEM at 200 kV in brightfield (BF), weakbeam darkfield (WBF) and selected area diffraction (SAD) modes. Normal brightfield images are produced using the transmitted spot to produce the brightest image possible.

Figure 11A:
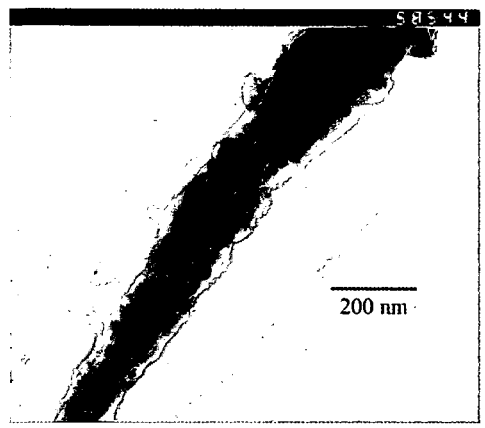
FIGS. 11A-11C show TEM micrographs of a single collagen fibril mineralized via a HA PILP phase.
Figure 11B:
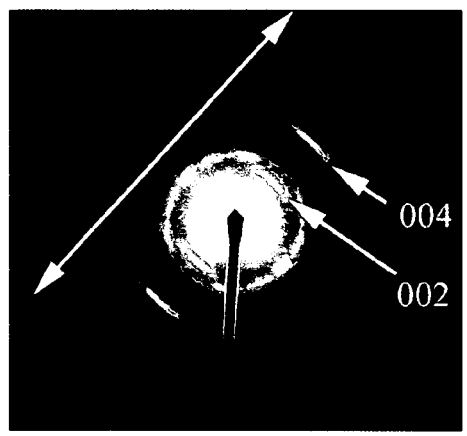

When a crystal phase is present, all of the planes that are parallel to the electron beam will diffract, thus creating diffraction patterns, such as those observed in FIG. 11B. When an objective aperture is placed over a diffraction spot (diffraction plane), the only electrons that are available for imaging are those originating from that plane. This converts a BF image into a PMDF image, in which the only crystals of the image that are illuminated are those that created the selected diffraction spot.

Samples were also prepared for scanning electron microscopy (SEM) by allowing whole samples to dry in air, mounting the dried samples on an aluminum stub covered in double-sided copper tape, and then sputter coating the stub with either a Au/Pd or amorphous carbon film. The samples were then analyzed using either a 6400 JEOL SEM or a 6330 JEOL FEGSEM at 15-20 kV. Elemental x-ray analysis (EDS) was performed on the mineralized sample with a Link-ISIS which was attached to both SEMs.

HA has a hexagonal crystal structure, which is best described by Miller Indices using the 4 coordinate axis, and therefore the directions are not mutually perpendicular to planes as occurs in cubic systems (Materials Science and Engineering: An Introduction; $5^{th}$ Edition, William D. Callister, Jr., John Wiley & Sons, Inc., 2000, chapter 3, pp. 30-65). The only directions that are mutually perpendicular are the {001} family of planes. The structure factor of the (001) plane does not allow it to appear in reciprocal space, and only the higher order (002) and (004) spacings are diffracted, but the [001] direction is always reported for the growth direction of HA in bone. As for the period listed in the (21.1) ring, it was done to show that true hexagonal nomenclature should be reported when using the 4 coordinate system to indicate a crystallographic plane. The (002) and (004) are higher order reflections of the basal planes of HA, and thus the third number (which is represented by a period in the (21.1) plane) is implied.

Figure 10A:
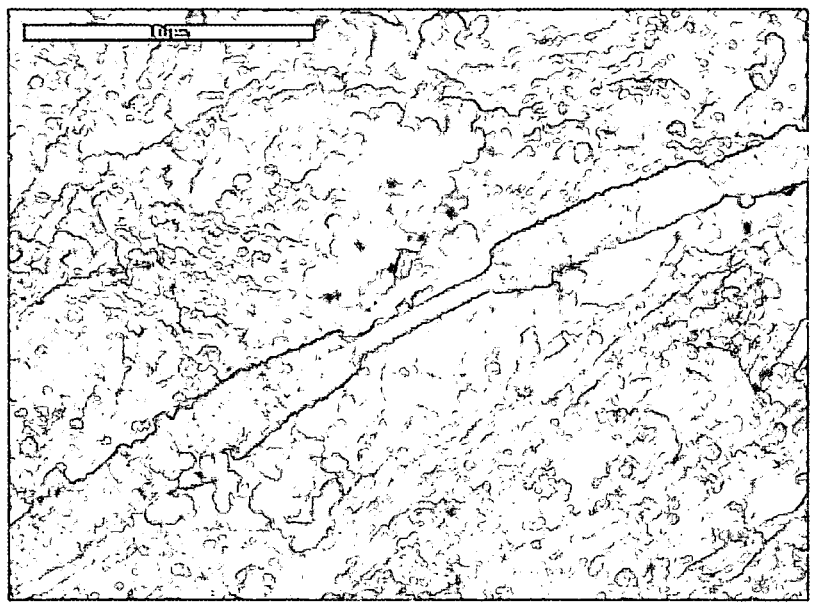
FIGS. 10A and 10B show SEM micrographs of type-I collagen sponge mineralized with hydroxyapatite (HA) mineral via the PILP process.
Figure 10B:
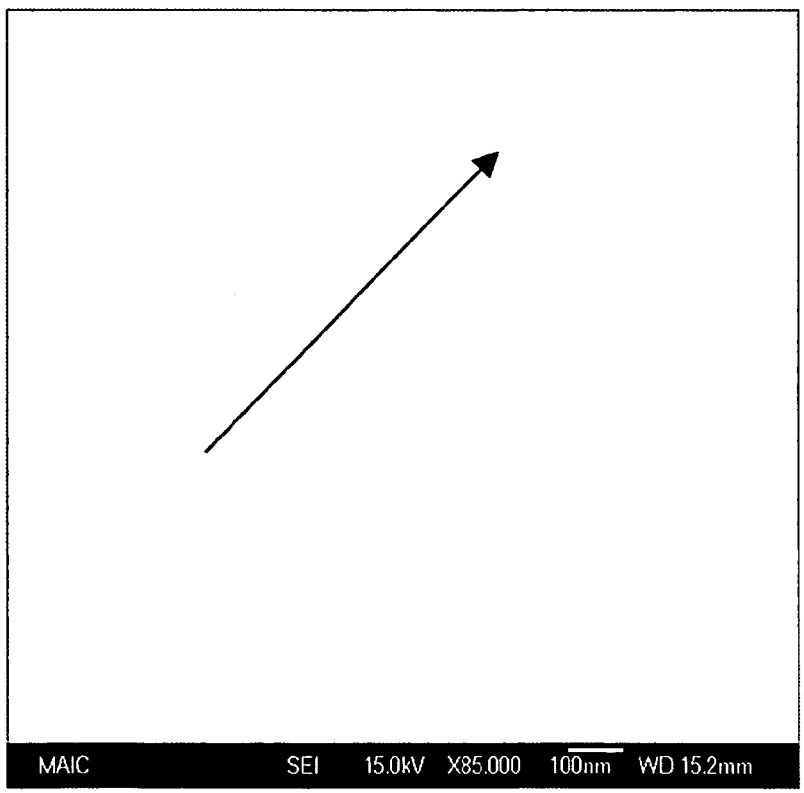

The present inventors have shown that collagen/HA composites can be created in which each individual collagen fibril is fully encased and infiltrated with mineral through the PILP phase, as shown in FIG. 10A. From the SEM micrographs it is not readily apparent as to the orientation of the HA in the collagen. Using a field-emission SEM (FEGSEM), higher resolution images of mineralized collagen fibrils have been obtained which show the platy/needle-like crystals oriented along the long axis of the collagen fibril, as shown in FIG. 10B. While the higher magnification images suggest that the mineral is aligned, it does not automatically provide crystallographic orientation. Using transmission electron microscopy (TEM), the present inventors have produced data showing that this mineral is indeed aligned in the [001] direction along the long axis of the collagen fibrils, similar to the mineral crystals found in bone.

Using transmission electron microscopy (TEM), the present inventors have been able to isolate a single collagen fibril mineralized with HA PILP phase (as shown in FIG. 11A). Although the mineral is not easily visualized in the brightfield image, using selected area diffraction of the middle of the fiber yields a diffraction pattern identified as HA (as shown in FIG. 11B). More importantly, the arcs for the 002 and 004 reflections are observed, meaning that the crystals are aligned parallel (c-axis of HA) to the long axis of the collagen fibril, such as is observed for mineral in bone.

Figure 12:
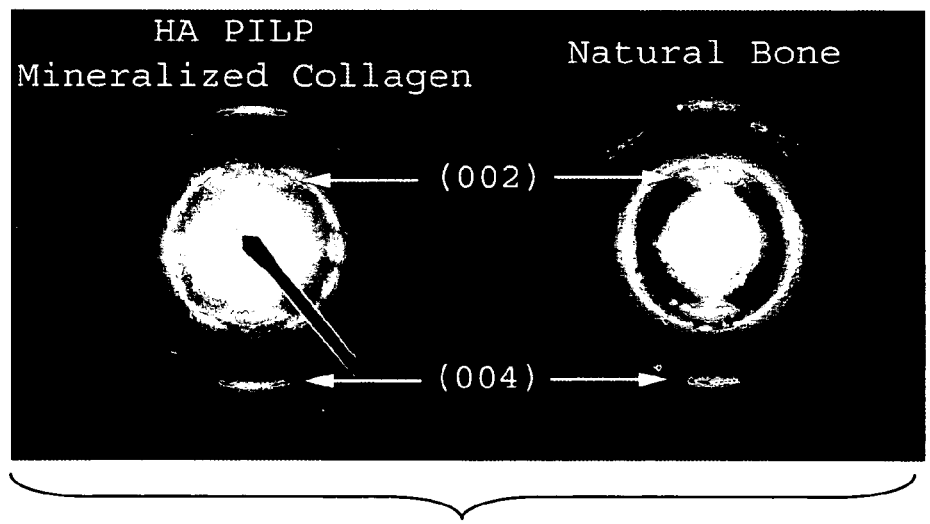
FIG. 12 shows SAD patterns derived from mineralized collagen samples. The left panel of FIG. 12 is the diffraction pattern from HA PILP mineralized collagen of the present invention. The right panel of FIG. 12 is a SAD diffraction pattern from a 50 year old male femur (after Ziv, V., et al., *Microscopy Research and Technique*, 1996, 33(2):203-213). Note how the patterns are identical, from the arcing of the (002) and (004) planes, which are aligned along the long axis of the collagen fibril, to the (112) diffraction ring just past the (002) diffraction spot. Note-a diffraction pattern containing arcs indicates slight mis-alignment of crystal planes, as compared to a spot pattern that is seen for single-crystalline materials.

While this diffraction pattern itself is intriguing data, what makes it most impressive is that it is identical, from the (21.1) diffraction ring to the arcing of the (002) and (004) diffraction planes, to mineralized collagen in bone. FIG. 12 shows a side-by-side comparison of diffraction data from the mineralized collagen fibril of the present invention to that of natural bone. It is important to note that while researchers have observed collagen to diffract x-rays due to its anisotropic orientation (yielding arc patterns typical of oriented fibrous materials), the small scale of isolated collagen fibers that is used for electron diffraction is not sufficient to diffract electrons, as is seen in FIG. 9B of an SAD pattern of collagen fibers prior to mineralization. Therefore, it can be concluded that the diffraction pattern in FIG. 11B could not be from the collagen by itself. As mentioned, the HA mineral phase is not easily observed within the collagen fibril. This was easily overcome using Poor Man's darkfield (PMDF), a technique that uses only the electrons diffracted from selected planes to image a sample.

Figure 11C:
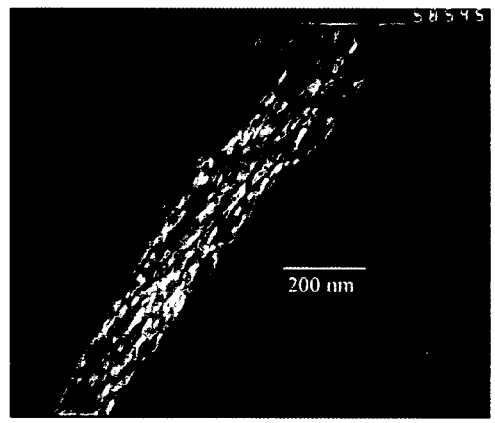
Figure 13A:
FIGS. 13A-13C show electron micrographs of mineralized collagen fibrils.
Figure 13C:
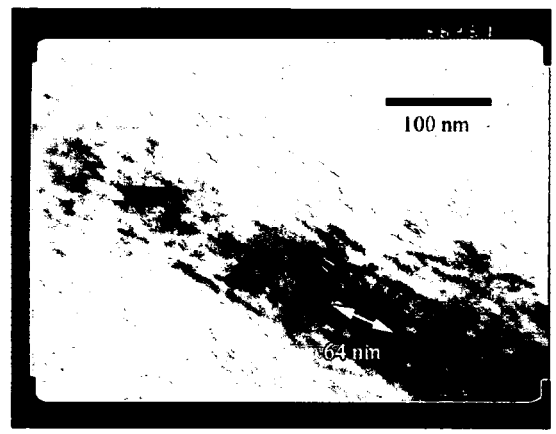
Figure 13B:
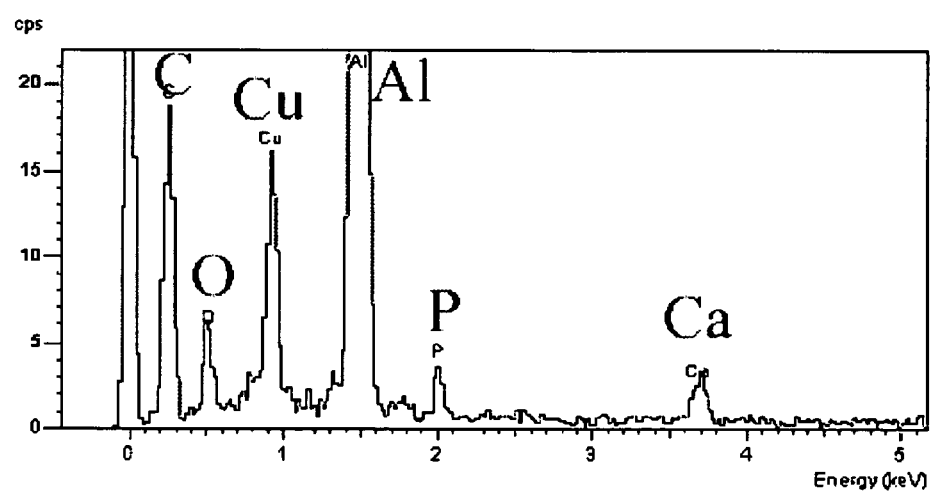

Placing the objective aperture over the (002) and then imaging using PMDF demonstrates that long platy/needle-like crystals oriented with the long axis of the collagen fibril (as shown in FIG. 11C). This PMDF data, combined with the extreme similarity of the diffraction patterns between the sample of the invention and natural bone confirms that this is indeed the HA phase of calcium phosphate. The only remaining question is whether or not this is actually mineralized collagen or if it is simply HA crystals. Two pieces of evidence refute any claims to this challenge. The first piece of evidence is that in SEM images of this exact region, platy/needle crystals cannot be discerned (as shown in FIG. 13A) but instead, a non-descript fiber of diameter ~150 nm with smooth surfaces is seen, indicating that the needle-like crystals observed in PMDF are intrafibrillar (EDS analysis on this bundle confirms the presence of Ca, P, and O (as shown in FIG. 13B)). The second piece of evidence is that in the same bundle of mineralized collagen, in which the mineralized fiber in FIGS. 11A and 11B was found, there was a section of fibers that displayed a faint banded pattern that matches with the 64 nm banding pattern of collagen (as shown in FIG. 13C), thereby confirming that the remainder of the bundle is mineralized collagen.

This data suggests that after mineralizing type-I collagen via a polymer-induced liquid-precursor (PILP) process (CaP variety), the morphology of mineralized collagen tissues in bone and teeth (at the nanostructural level) has been recreated. At early times in the mineralization process, the present inventors have shown amorphous PILP droplets in association with type-I collagen, which suggests that during synthesis these droplets are being drawn into the collagen via capillary action. At later times, as the amorphous PILP phase begins to crystallize, the collagen-mineral interface leads to orientation of the HA crsytals in the [001] direction (along its c-axis), leaving it intrafibrillarly mineralized with the classic "deck-of-cards" architecture described for bone (Weiner & Traub). EDS analysis of this fibril confirms the presence of Ca, P, and O within the fibril. PMDF, with the (002) HA planes highlighted, demonstrates that long platy/needle-like crystals are oriented along the long axis of the collagen. Finally, as the inventors' previous SEM data have shown, the exact mineralized collagen fibril analyzed for the TEM orientation data has a non-descript appearance, meaning that the platy mineral is intrafibrillarly mineralized within the 150 nm diameter fibril.

EXAMPLE 4

Mineralization of Polymeric, Fluid-Swellable Materials

The experiments described above with respect to collagen were similarly carried out on SCOTCH BRITE sponges.

Figure 14:
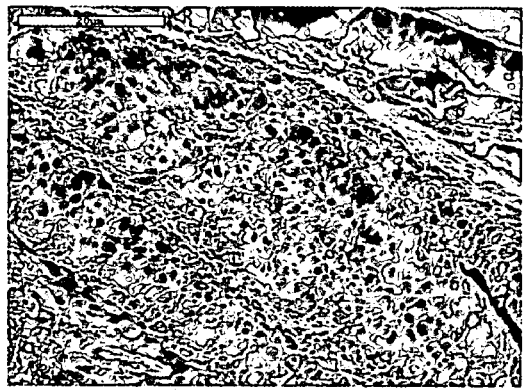
FIG. 14 shows an SEM of a SCOTCH BRITE sponge that has not been introduced to mineralizing solutions. This household sponge has micropores on the order of 0.75 microns-2.0 microns in diameter.
Figure 15:
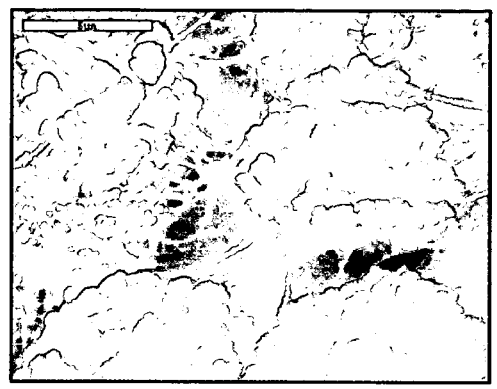
FIG. 15 shows an SEM of a CELLAGEN sponge (reconstituted bovine Type-I collagen) that has been mineralized using the process of the subject invention. The fibers are collagen and the mounds are collagen fibers coated in calcium carbonate.
Figure 16:
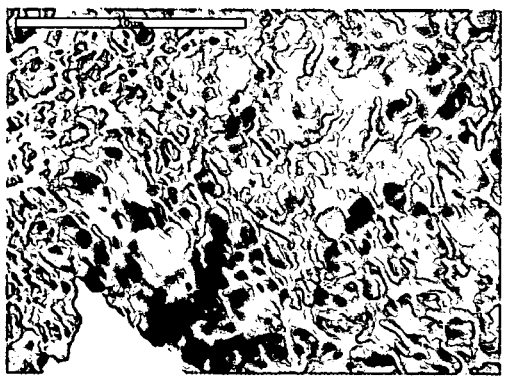
FIG. 16 shows an SEM of a SCOTCH BRITE sponge that has been mineralized using the process of the subject invention. The sponge has been coated with non-equilibrium morphology calcium carbonate, thus clogging some of the pores.
Figure 17:
FIG. 17 is an SEM of a CELLAGEN sponge that has been mineralized using the process of the subject invention. The sample was mineralized four times. Specifically, the sample was run for three days and the mineralizing solution was subsequently refreshed (the equivalent of one mineralization). The sample was then placed in a 0.1N HCl solution to etch away the surface coating of calcium carbonate. The large bundle of fibers in the middle of the picture shows how the whole bundle may have been coated (hence, the end which still seems to be coated) and the acid etch preferentially left behind bands of calcium carbonate.
Figure 18:
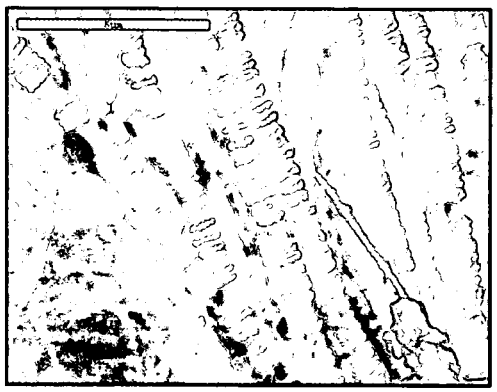
FIG. 18 shows an SEM of a CELLAGEN sponge that has been mineralized using the process of the subject invention. The sample was mineralized five times. Specifically, the sample was run for three days and the mineralization solution was subsequently refreshed (the equivalent of one mineralization). The sample was then placed in a 0.1 N HCl solution to etch away the surface coating of calcium carbonate. Again, all of the fibers appear to have been coated and the acid etch preferentially etched away the excess calcium carbonate, leaving behind banded calcium carbonate that was protected from the etchant by the surrounding collagen fiber.
Figure 19:
FIG. 19 shows an SEM of a CELLAGEN sponge that has been mineralized using the process of the subject invention. The sample was mineralized five times. Specifically, the sample was run for three days and the mineralization solution was subsequently refreshed (the equivalent of one mineralization). The sample was then placed in a 10% bleach solution to etch away the organic material, specifically collagen. With the collagen removed, it can be seen that the calcium carbonate that remains had totally infiltrated the collagen (the perpendicular bands of mineral span completely across the pre-existing fibers).

FIG. 14 shows an SEM of a SCOTCH BRITE sponge that has not been introduced to mineralizing solutions. It has micropores on the order of 0.75 microns-2.0 microns in diameter. FIG. 16 shows an SEM of a SCOTCH BRITE sponge that has been mineralized using the process of the subject invention. The sponge has been coated with non-equilibrium morphology calcium carbonate, thus clogging some of the pores. Specifically, the sponge shown in FIG. 16 was mineralized four times (three days for each mineralization interval at 12 mM $CaCl_2$, 200 μg/mL PAA (5100 m.w.), vapor diffusion of ammonium carbonate). After each interval, the solution was refreshed. Although the calcium carbonate coating is not obvious in the SEM of FIG. 16, energy dispersive spectroscopy (EDS) measurements have been performed which ensure that the sponge was mineralized with calcium carbonate. In addition, whereas the unmineralized sponge would be extensively damaged by the electron beam from the EDS measurements (as organic materials do not conduct electricity with great ease), the mineralized samples, as the one shown in FIG. 16, resisted electron beam damage due to the inorganic coating.

EXAMPLE 5

In Vitro Cellular Response to Mineralized CELLAGEN

Rat bone marrow stem cells were harvested and seeded into 168 $cm^2$ culture flasks in standard culture media (DMEM supplemented with 10% FBS, 1% Penicillin/Streptomycin and dextrose). Cells were cultured for 14 days and media was changed on every fourth day. On day 14, the cells were trypsinized, counted and seeded in four 168 cm2 tissue culture dishes at a density of 1E6 cells/$cm^2$. Stem cells in three culture dishes were supplemented with OS media (Standard media+100 nM Dexamethasone+10 nM b-Glycerophosphate+0.05 mM Ascorbic acid) for an eight-day period to initiate and accelerate stem cell differentiation into osteoblasts. The remaining stem cells were supplemented with standard culture media to serve as controls.

Following this eight-day supplementation period, the osteoblasts and stem cells were trypsinized and counted with a hemocytometer. Osteoblasts and undifferentiated stem cells were seeded into three wells each of a 24-well plate at a density of 1.6E4 cells/well. The cells were allowed to attach to the base of each well for a 3.5-hour period at which time an alkaline phosphatase (ALP) assay was performed to evaluate the extent of differentiation to osteoblast-like cells elicited by the OS media. Scaffolds composed of unmineralized CELLAGEN (A, n=6), mineralized CELLAGEN without polymer (B, n=6), and mineralized CELLAGEN with polymer (C, n=6) were sterilized using 2.5 Gy gamma irradiation. Two scaffolds per matrix type were reserved for negative control (no cells) SEM analysis; the remaining 4 scaffolds per matrix type were seeded with cells. Osteoblasts were seeded at a density of 4E4 cells/scaffold and aliquoted onto each scaffold in a total of 80 ul. All scaffolds were placed in separate 2 cm wells of a 24 well plate. Osteoblasts were allowed to adhere to the scaffolds for a period of 3.5 hours, at which time the cell-containing scaffolds were removed and placed into new 2 $cm^2$ wells. The number of cells remaining in the 2 $cm^2$ incubation wells after removal of the scaffolds were quantified using a crystal violet assay. The cell-containing scaffolds were then supplemented with standard media and kept in a 37° C. incubator for a seven-day period. After 12 hours and 7 days, osteoblasts were fixed in Karnovsky's solution and prepared for SEM imaging.

MSCs differentiated into the osteoblast lineage when cultured with OS media as confirmed with the ALP assay. After scaffold exposure to 4E+04 cells/scaffold for 3.5 hours, 25% of the cells adhered to the unmineralized CELLAGEN scaffold whereas 50% of the cells adhered to the mineralized CELLAGEN scaffold with or without polymer (FIG. 21).

Absorbance values were compared to a previously constructed standard curve for determination of cell number. Initial comparisons with the standard curve were used to indicate the number of cells in the base of each 2 $cm^2$ well, and represent the number that had not successfully adhered to the scaffolds. The difference between this number and 4E+04 is the total number of cells that had successfully adhered to each matrix. Since all scaffolds that received osteoblasts were seeded simultaneously, the numbers given above were assumed to be valid for all scaffolds even though only 2 per treatment underwent this preliminary crystal violet stain and cell number determination.

Figure 22A:
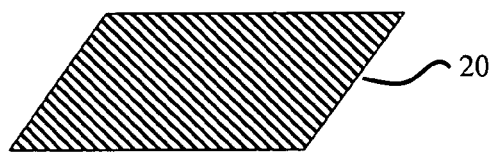
FIGS. 22A-22E show materials and methods for producing individually mineralized films of the present invention.
Figure 22B:
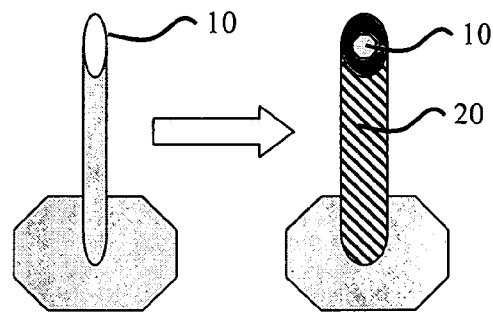
Figure 22C:
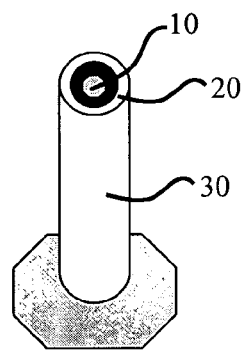
Figure 22D:
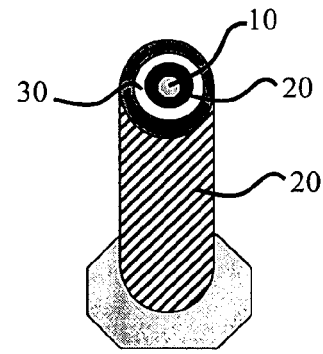

Qualitative SEM imaging indicated adherence of osteoblasts onto the mineralized matrices (FIG. 22A). The presence of calcified matrix nodules (FIG. 22B) suggests interaction of differentiated osteoblasts with the scaffold. Positive identification of osteoblast within the matrix will be confirmed in future studies by quantifiable methylthiazol tetrazolium (MTT) proliferation assays. FIG. 21 summarizes results of cell adhesion to the mineralized CELLAGEN scaffolds. The mineralized scaffold without polymer (containing blocky calcite crystals) showed similar cell adhesion.

EXAMPLE 6

Organic/Inorganic Composites Having Nanostructured Architecture of Bone

Using a PILP phase, the process of the present invention provides a means for generating intrafibrillar mineralization of organic substrates, such as collagen, yielding composites that are similar in composition and architecture as bone. However, the hierarchical levels of structure found in bone, which result from cellular processes, are difficult to duplicate synthetically. Therefore, the present inventors have developed methods to impart some of the more significant features of those of natural bone, such as microporosity for cell infiltration, and laminated structures for enhanced mechanical properties, to the composites of the present invention.

Compact bone has numerous osteonal canals. These osteons are comprised of concentric lamella of mineralized collagen (Weiner S, Traub W, Wagner H D [1999] *Journal of Structural Biology* 126:241-255). As previously indicated, the ability to create such a complex structure in vitro by artificial mineralization processes is not possible. However, the present invention can overcome this hurdle. Using the process of the invention, layers of mineralized collagen films can be individually mineralized via the PILP mechanism. These layers, whether composed of pre-oriented or isotropically arranged collagen fibers, can then be cut into desired dimensions and wrapped around a mandrel 10. As shown in FIGS. 22A-22E, the mandrel 10, which represents the space occupied by the canal in natural osteons, will be used as a mechanical support (or form) in which to wrap the mineralized (or pre-mineralized) films or sheets 20. The mandrel 10 can be composed of a bioresorbable material, in which case it can remain as part of the composite. Alternatively, the mandrel 20 can be composed of a non-resorbable material, in which case it can be removed before implantation into a patient.

Figure 22E:
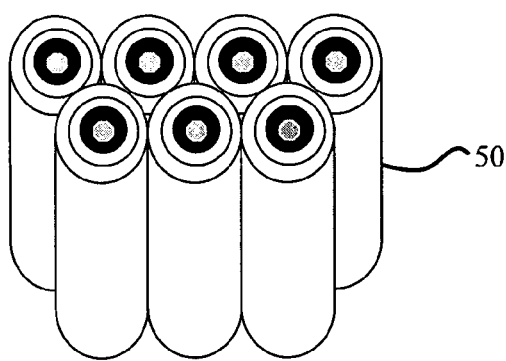

Since the mineralized layers do not have any natural tacticity, a coating of bioresorbable adhesive 30 (e.g., polylactic acid, polyglycolic acid) can be applied between each individual layer wrapping. Alternatively, a cementations adhesive layer can be applied, either via the PILP process of the present invention, or other bone paste materials, mimicking that of the "cement line" in natural bone. Once each individual osteon 50 is fabricated, many osteons 50 can be adhered to one another, as shown in FIG. 22E, to form a much larger composite resembling the hierarchical structure of osteonal bone.

The organic fluid-swellable, fibrous matrix of the composites of the present invention can be made so as to be oriented to achieve, for example, a parallel orientation, using flow fields, electric fields, magnetic fields, or combinations thereof (Murthy N. S. [1984] *Biopolymers* 23:1261-1267; Oh Y. R. et al. [1992] *J. Chem. Eng. Jpn.* 25:243-250; Dickinson R. B. et al. [1994] *Ann. Biomed Eng.* 22:342-356; Tranguillo R. T. et al. [1996] *Biomaterials* 17:349-357; Guido S. et al. [1993] *J. Cell. Sci.* 105:317-331). During the process of the invention, such oriented substrates act as templates for deposition of the amorphous mineral precursor into the fluid-swellable matrix. Therefore, an oriented nanocrystalline hydroxyapatite phase can be achieved, for example. Such a composite would more closely mimic the structure of parallel-fibered bone, providing important advantages such as tailored mechanical properties and contact guidance of cells during healing.

Figure 23A:
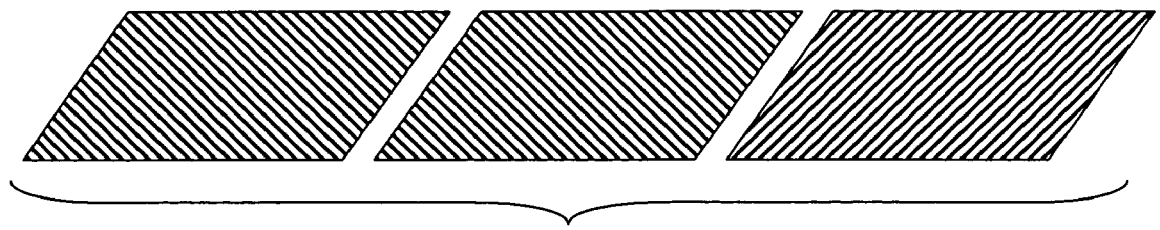
FIGS. 23A-23C show mineralized films of the present invention, which can be adhered to one another in an alternating orientation, to form a cross-ply architecture.
Figure 23B:
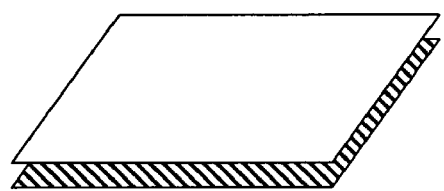
Figure 23C:
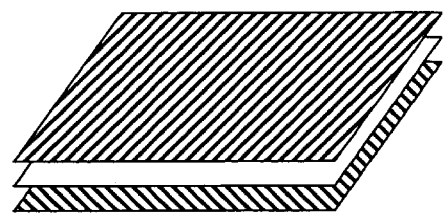

In one embodiment, the mineralized collagen sheets 20 can be adhered to one another by bioresorbable adhesives, such as those previously described, with each mineralized collagen layer placed in alternating orientation, to for a cross-ply architecture, as shown in FIGS. 23A-C.

EXAMPLE 7

Porous Organic/Inorganic Composites

The ends of long bones have a much different macro-structure than that of the central shaft area of long bones. Underlying the cortical bone is trabecular or cancellous bone, which has a porous structure (Weiner S et al. [1999] *Journal of Structual Biology*, 126:241-255).

This type of macro-structure can be achieved using the process of the subject invention, in combination with certain processing techniques known in the art that can be applied to the organic matrix before, during, or after mineralization. For example, using a freeze-dried or direct templating process, collagen scaffolds with desired porosity can be produced with a range of pore sizes. Pore sizes in the range of about 50 to 500 microns (preferably, 100 to 200 microns) are commonly used to enhance cell infiltration (osteoconductive material), which provides accessibility to the cells for remodeling the synthetic substitute into natural bone. These collagen scaffolds can then be mineralized via the PILP mechanism of the present invention in order to create a hard porous composite. Porous scaffolds can also be produced using organic substrates other than collagen.

Due to the size of the pores, larger homogenous structures can be prepared, which will enhance the capillary action of the secondary liquid phase produced by the PILP mechanism, allowing the precursor phase to be drawn further into the interior of the composite, thus allowing for complete mineralization.

Porosity of the composite can also be introduced and/or controlled by a variety of techniques, including freeze drying techniques; incorporation of porogens (e.g., salts or other solubilizing substances that are removed subsequent to matrix formation); phase segregation of matrix media comprised of multiple phases (e.g., block copolymers or immiscible blends), e.g., using phase segregating polymers; high temperature sintering; and supercritical processing (creation of matrix in a supercritical state, which generates pores as the supercritical conditions are removed, most commonly as reduction in pressure or temperature) (Nehrer, S., et al. [1999] *Biomaterials*, 19:2313-2328; Zhang, R. et al. [1999] *J. Biomed. Mater. Res.* 44:446-455).

As indicated above, in order to obtain large samples with controlled porosity, a freeze-drying technique can be used. The porosity is preferably a continuous network to provide an open path for cells to travel to the center of the implant during healing. In addition, the use of the freeze-drying technique will result in a dense collagen scaffold such that subsequent mineralization will lead primarily to intrafibrillar mineralization, without mineralization of interfibrillar voids that would generate brittle regions of pure mineral phase. The intrafibrillar mineralization should lead to a nanostructured composite with enhanced mechanical properties that better mimic the properties of natural bone.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A method for treating a bone defect comprising:
   applying an organic/inorganic composite to the site of the bone defect;
   wherein said organic/inorganic composite comprises a fluid-swellable, fibrous matrix and an inorganic mineral, and said organic/inorganic composite is formed by contacting an amorphous inorganic liquid-phase mineral precursor with said fluid-swellable, fibrous matrix, wherein said amorphous inorganic liquid-phase mineral precursor is absorbed into said fluid-swellable, fibrous matrix and coats and infiltrates, and subsequently hardens and crystallizes within, said fluid-swellable, fibrous matrix.

2. The method according to claim 1, wherein said organic/inorganic composite is applied as an injectable liquid, a film, a malleable putty, a malleable paste, a particulate, or a molded or preformed solid.

3. The method according to claim 1, wherein said fluid-swellable, fibrous matrix comprises a material selected from the group consisting of collagen, elastin, chitin, chitosan, and cellulose.

4. The method according to claim 1, wherein said inorganic mineral is selected from the group consisting of calcium phosphate, calcium carbonate, hydroxyapatite, strontium carbonate, calcium sulfate, calcium oxalate, magnesium-bearing calcium carbonate, and magnesium-bearing calcium, or combinations thereof.

5. The method according to claim 1, wherein said organic/inorganic composite further comprises a biologically active agent within said organic/inorganic composite.

6. The method according to claim 1, wherein said organic/inorganic composite is porous.

7. The method according to claim 1, wherein said fluid-swellable, fibrous matrix is biocompatible and bioresorbable.

8. The method according to claim 1, wherein said fluid-swellable, fibrous matrix is in the form of a scaffold, and wherein said scaffold is seeded with cells.

9. The method according to claim 8, wherein said cells are selected from the group consisting of bone marrow stem cells, osteoblasts, osteoclasts, osteocytes, blood cells, epithelial cells, odontoblast, ameloblasts, and neural cells, or combinations thereof.

10. The method according to claim 1, wherein said fluid-swellable, fibrous matrix is a film.

11. The method according to claim 1, wherein said organic/inorganic composite comprises a plurality of said fluid-swellable, fibrous matrices arranged as lamellae.

12. The method according to claim 11, wherein said lamellae are arranged concentrically around a central void for passage of endogenous or exogenous cells.

13. The method according to claim 1, wherein said organic/inorganic composite comprises a plurality of said fluid-swellable, fibrous matrices, and wherein said organic/inorganic composite further comprises an adhesive layer between each of said fluid-swellable, fibrous matrices.

* * * * *

UNITED STATES PATENT AND TRADEMARK OFFICE
CERTIFICATE OF CORRECTION

PATENT NO. : 7,547,449 B2
APPLICATION NO. : 11/433725
DATED : June 16, 2009
INVENTOR(S) : Laurie B. Gower et al.

It is certified that error appears in the above-identified patent and that said Letters Patent is hereby corrected as shown below:

Column 12:
Line 31, "α2 collagen" should read --$\alpha_2$ collagen--

Column 25:
Line 57, "2 cm" should read --2 $cm^2$--

Signed and Sealed this

Twenty-second Day of September, 2009

David J. Kappos
*Director of the United States Patent and Trademark Office*